(12) United States Patent
McEntire et al.

(10) Patent No.: US 11,850,214 B2
(45) Date of Patent: *Dec. 26, 2023

(54) ANTIVIRAL COMPOSITIONS AND DEVICES AND METHODS OF USE THEREOF

(71) Applicant: SINTX TECHNOLOGIES, INC., Salt Lake City, UT (US)

(72) Inventors: Bryan J. McEntire, Salt Lake City, UT (US); Ryan M. Bock, Salt Lake City, UT (US); Bhajanjit Singh Bal, Salt Lake City, UT (US)

(73) Assignee: SINTX Technologies, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/230,402

(22) Filed: Apr. 14, 2021

(65) Prior Publication Data

US 2021/0228625 A1 Jul. 29, 2021

Related U.S. Application Data

(63) Continuation-in-part of application No. 16/550,605, filed on Aug. 26, 2019, now Pat. No. 11,192,787.

(60) Provisional application No. 62/727,724, filed on Sep. 6, 2018, provisional application No. 62/800,034, filed on Feb. 1, 2019, provisional application No. 63/143,370, filed on Jan. 29, 2021.

(51) Int. Cl.
| | | |
|---|---|---|
| *A61K 33/00* | (2006.01) | |
| *A61K 8/25* | (2006.01) | |
| *A61Q 11/00* | (2006.01) | |
| *A61P 31/16* | (2006.01) | |
| *A61L 2/23* | (2006.01) | |

(52) U.S. Cl.
CPC ............... *A61K 33/00* (2013.01); *A61K 8/25* (2013.01); *A61L 2/23* (2013.01); *A61P 31/16* (2018.01); *A61Q 11/00* (2013.01)

(58) Field of Classification Search
None
See application file for complete search history.

(56) References Cited

U.S. PATENT DOCUMENTS

| | | | | |
|---|---|---|---|---|
| 6,302,913 B1‡ | 10/2001 | Ripamonti | ........... | A61C 8/0012 623/16.11 |
| 7,776,085 B2‡ | 8/2010 | Bernero | ..... | A61F 2/38 623/2.32 |
| 9,925,295 B2‡ | 3/2018 | McEntire | ............... | C04B 35/597 |
| 10,806,831 B2‡ | 10/2020 | McEntire | ................ | A61L 27/50 |
| 2009/0320172 A1 | 12/2009 | Slate et al. | | |
| 2010/0040655 A1‡ | 2/2010 | Ren | ..... | A41D 13/1192 424/402 |
| 2013/0236854 A1‡ | 9/2013 | McEntire | ............. | A61C 8/0013 433/173 |
| 2013/0302509 A1‡ | 11/2013 | McEntire | ................ | A61L 27/54 427/2.24 |
| 2016/0339144 A1‡ | 11/2016 | McEntire | ............. | A61L 27/025 |
| 2017/0197014 A1‡ | 7/2017 | McEntire | ............. | A61L 31/022 |

FOREIGN PATENT DOCUMENTS

| | | | |
|---|---|---|---|
| CN | 107926975 A | ‡ | 4/2018 |
| CN | 107926975 A | | 4/2018 |
| JP | 2009526828 A | | 7/2009 |
| JP | 2015516239 A | | 6/2015 |
| JP | 2020019677 A | | 2/2020 |
| WO | 2011067005 A1 | | 6/2011 |

OTHER PUBLICATIONS

Pezzotti et al.( Rapid inactivation of SARS-CoV-2 by silicon nitride, copper, and aluminum nitride bioRxiv (2020) 1-16, 2020). (Year: 2020).*
Adiga et al., Nanoporous membranes for medical and biological applications, 2009, Nanomed Nanobiotechnology, vol. 1, No. 5, pp. 568-581 (Year: 2009).‡
Extended European Search Report issued in corresponding Application No. 19856613.5 dated May 2, 2022, 10 pages.
First Examination Report issued in corresponding Indian Application No. 202137015785, 7 pages.
Office Action in related U.S. Appl. No. 17/230,395 dated Oct. 28, 2022, 11 pages.
Office Action in related U.S. Appl. No. 17/230,284 dated Oct. 28, 2022, 10 pages.
Pezzotti et al., Rapid Inactivation of SARS-COV-2 by Silicon Nitride, Copper, and Aluminum Nitride, 2020, 16 pages.
U.S. Patent and Trademark Office, Final Office Action, U.S. Appl. No. 17/230,284, dated Apr. 6, 2023, 9 pages.
U.S. Patent and Trademark Office, Non-Final Office Action, U.S. Appl. No. 17/230,395, dated Apr. 6, 2023, 11 pages.
IP Australia, Examination Report No. 2 for Standard Patent Application, Application No. 2019336133, dated May 3, 2023, 5 pages.
China National Intellectual Property Administration (CNIPA), First Office Action, Application No. 201980058291.0, dated Mar. 8, 2023, 18 pages.
Japan Patent Office, Notice of Reasons for Rejection, Application No. 2021-510805, dated Jan. 24, 2023, 5 pages.

\* cited by examiner
‡ imported from a related application

*Primary Examiner* — Alton N Pryor
(74) *Attorney, Agent, or Firm* — Polsinelli PC

(57) ABSTRACT

Described herein are antiviral compositions and apparatuses and methods of use thereof to inactivate a virus in contact with the composition or apparatus. The composition and/or apparatus include silicon nitride at a concentration of 1 wt. % to 15 wt. % and the silicon nitride inactivates at least 85% of the virus in contact with the composition and/or apparatus.

13 Claims, 25 Drawing Sheets

FIG. 10

NP + F-actin

Viral NP

F-actin

NP + F-actin

Viral NP

F-actin

Step 1: SARS-CoV-2 virus was diluted in media

Step 2: 4mL diluted virus was added to tubes containing silicon nitride at 20, 15, 10 or 5% (w/v)

Step 3: Tubes were vortexed for 30s to ensure adequate contact and then placed on a tube revolver for either 1m, 5m, or 10m (virus only control was incubated for the maximum 10m)

Step 4: At each time point, the samples were centrifuged, and the supernatant was collected and filtered through a 0.2 μm filter

Step 5: Clarified supernatant was used to perform plaque assays; samples were serially diluted (10-fold) and added to fresh Vero for 1h incubation, rocking every 15m, before adding an agarose medium overlay and incubating for 48h. After 48h incubation, cells were fixed with 10% FA and stained with Crystal Violet for counting.

FIG. 23

ANTIVIRAL COMPOSITIONS AND DEVICES AND METHODS OF USE THEREOF

CROSS-REFERENCE TO RELATED APPLICATIONS

This application is a Continuation-in-Part of U.S. application Ser. No. 16/550,605, filed Aug. 26, 2019 that claims the benefit of U.S. Provisional Applications 62/727,724, filed Sep. 6, 2018 and 62/800,034, filed Feb. 1, 2019. This application also claims the benefit of U.S. Provisional Application No. 63/143,370, filed Jan. 29, 2021. The contents of all of which are entirely incorporated by reference herein.

FIELD

The present disclosure relates to antiviral compositions, systems, methods, and devices. More specifically, the disclosure relates to silicon nitride compositions, devices, and coatings for the inactivation of viruses.

BACKGROUND

The need for safe and reliable inactivation or removal of viruses is universal. There is a broad need to control the pathogens that affect human health. Not only is there a need for materials that possess antiviral properties for human medicinal therapies, but also for use as surface coatings and/or composites for various medical devices or equipment, examination tables, clothing, filters, masks, gloves, catheters, endoscopic instruments, and the like.

Severe acute respiratory syndrome coronavirus 2 (SARS-CoV-2), which is responsible for the COVID-19 pandemic, remains viable and therefore potentially infectious on several materials. One strategy to discourage the fomite-mediated spread of COVID-19 is the development of materials whose surface chemistry can spontaneously inactivate SARS-CoV-2.

Therefore, there is a need for safe and reliable methods to inactivate and kill viruses that may be applied to medical devices, equipment, clothing, or other systems which may have prolonged contact with the human body.

SUMMARY

Provided herein are embodiments of an antiviral composition comprising silicon nitride at a concentration of about 1 wt. % to about 15 wt. %, where the silicon nitride inactivates a virus in contact with the composition.

In some aspects, the virus may be in contact with the silicon nitride for a duration of at least 1 minute or at least 30 minutes. For example, the virus may be at least 85% inactivated after contact with the silicon nitride for at least 1 minute. The silicon nitride may be present at a concentration of less than or equal to 10 wt. %. The silicon nitride may be $\alpha$-$Si_3N_4$, $\beta$-$Si_3N_4$, SiYAlON, $\beta$-SiYAlON, SiYON, or SiAlON. The virus may be Influenza A or SARS-CoV-2. In some aspects, the composition is a slurry, suspension, gel, spray, paint, or toothpaste.

Further provided herein are embodiments of an antiviral apparatus comprising silicon nitride at a concentration of about 1 wt. % to about 15 wt. %, wherein the silicon nitride inactivates a virus in contact with the composition.

In some aspects, the virus may be in contact with the silicon nitride for a duration of at least 1 minute or at least 30 minutes. For example, the virus may be at least 85% inactivated after contact with the silicon nitride for at least 1 minute. The silicon nitride may be present at a concentration of less than or equal to 10 wt. %. The silicon nitride may be $\alpha$-$Si_3N_4$, $\beta$-$Si_3N_4$, SiYAlON, $\beta$-SiYAlON, SiYON, or SiAlON. The virus may be Influenza A or SARS-CoV-2. In some aspects, the apparatus may be a medical device, medical equipment, examination table, filters, masks, gloves, catheters, endoscopic instruments, or commonly-touched surfaces. The apparatus may be metallic, polymeric, and/or ceramic and the silicon nitride may be coated on or embedded in a surface of the apparatus.

Also provided herein are embodiments of a method of preventing transmission of a virus comprising: contacting an antiviral apparatus with the virus, where the apparatus comprises silicon nitride at a concentration of about 1 wt. % to about 15 wt. %.

In some aspects, the virus may be in contact with the silicon nitride for a duration of at least 1 minute or at least 30 minutes. For example, the virus may be at least 85% inactivated after contact with the silicon nitride for at least 1 minute. The silicon nitride may be present at a concentration of less than or equal to 10 wt. %. The silicon nitride may be $\alpha$-$Si_3N_4$, $\beta$-$Si_3N_4$, SiYAlON, $\beta$-SiYAlON, SiYON, or SiAlON. The virus may be Influenza A or SARS-CoV-2.

Other aspects and iterations of the invention are described more thoroughly below.

BRIEF DESCRIPTION OF THE DRAWINGS

Figure 10:
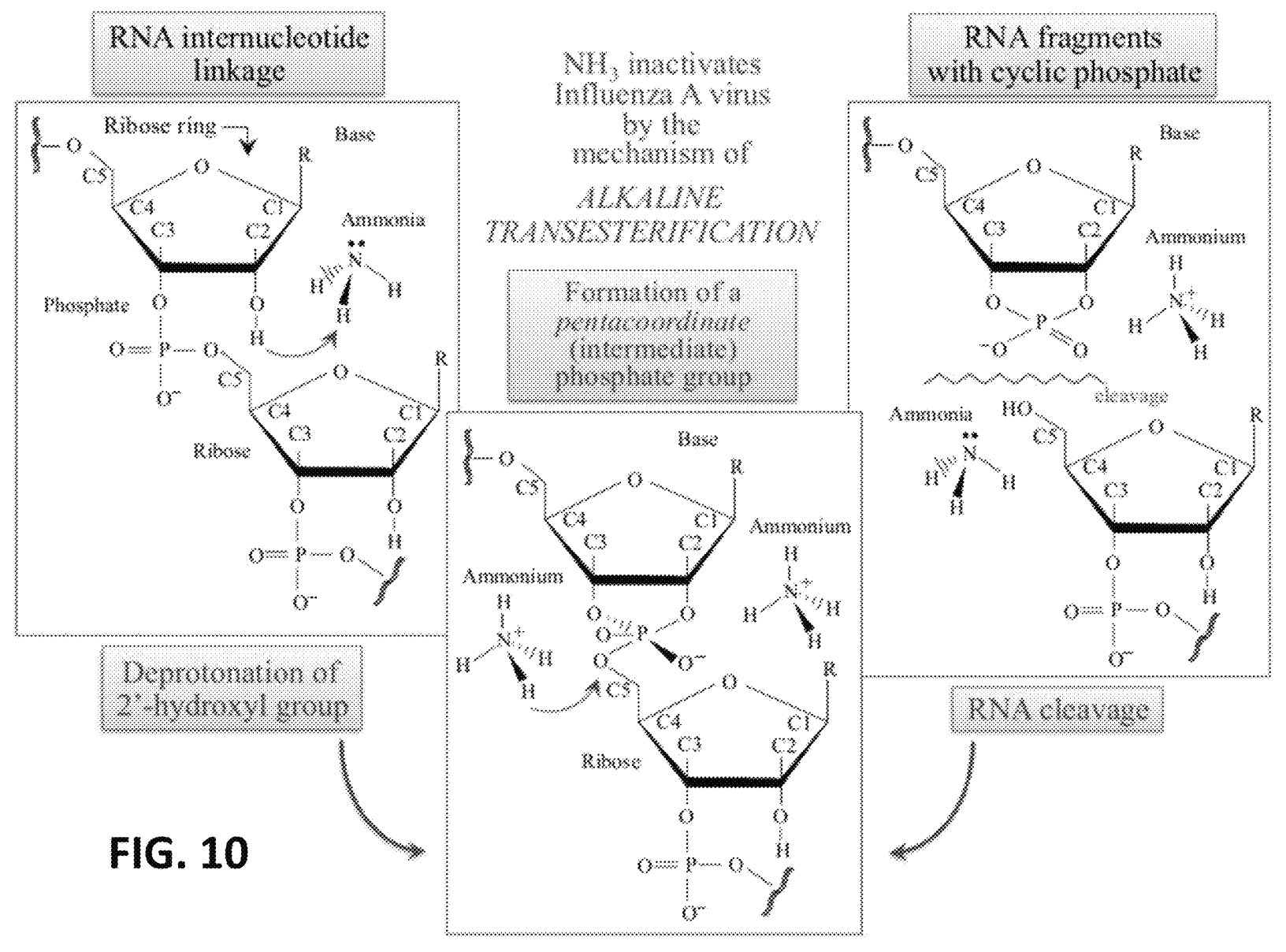

FIG. 10 shows $NH_3$ inactivates Influenza A virus by the mechanism of alkaline transesterification.

FIG. 17 shows a trimodal distribution of silicon nitride powder.

FIG. 19 shows a direct comparison of the viral titers before and after exposure of Influenza A to the $Si_3N_4$ powder for 30 minutes.

FIG. 22 shows a trimodal particle size distribution of silicon nitride powder.

FIG. 23 is an overview of the antiviral testing method.

DETAILED DESCRIPTION

Figure 1:
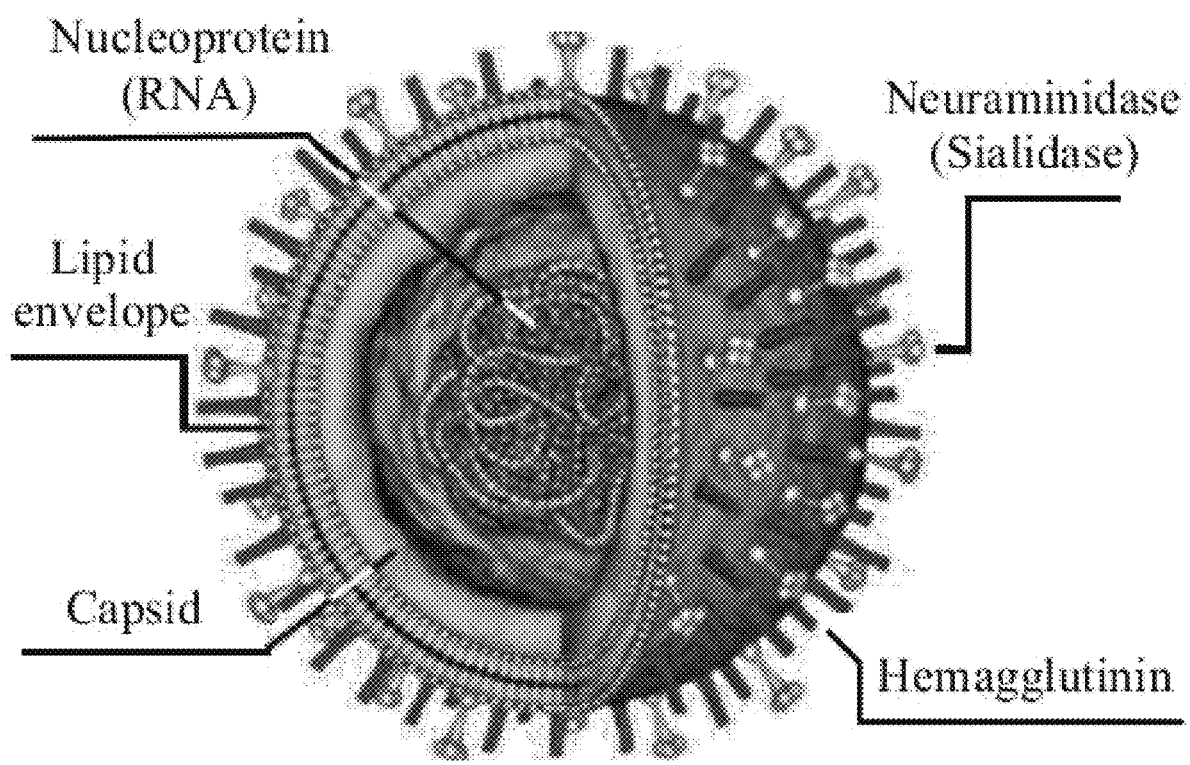
FIG. 1 is an illustration of the Influenza A virus.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description.

Several definitions that apply throughout this disclosure will now be presented. Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

As used herein, the terms "comprising," "having," and "including" are used in their open, non-limiting sense. The terms "a," "an," and "the" are understood to encompass the plural as well as the singular. Thus, the term "a mixture thereof" also relates to "mixtures thereof."

As used herein, "about" refers to numeric values, including whole numbers, fractions, percentages, etc., whether or not explicitly indicated. The term "about" generally refers to a range of numerical values, for instance, ±0.5-1%, ±1-5% or ±5-10% of the recited value, that one would consider equivalent to the recited value, for example, having the same function or result.

As used herein, the term "silicon nitride" includes $\alpha$-$Si_3N_4$, $\beta$-$Si_3N_4$, SiYAlON, $\beta$-SiYAlON, SiYON, SiAlON, or combinations thereof.

As used herein, "inactivate" or "inactivation" refers to viral inactivation in which the virus is stopped from contaminating the product or subject either by removing virus completely or rendering them non-infectious.

The terms "apparatus" or "component" as used herein include materials, compositions, devices, surface coatings, and/or composites. In some examples the apparatus may include various medical devices or equipment, examination tables, clothing, filters, personal protective equipment such as masks and gloves, catheters, endoscopic instruments, commonly-touched surfaces where viral persistence may encourage the spread of disease, and the like. The apparatus may be metallic, polymeric, and/or ceramic (ex. silicon nitride and/or other ceramic materials).

As used herein, "contact" means in physical contact or within close enough proximity to a composition or apparatus to be affected by the composition or apparatus.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Provided herein are antiviral devices, compositions, and apparatuses that include silicon nitride ($Si_3N_4$) for the inactivation of viruses. Silicon nitride possesses a unique surface chemistry which is biocompatible and provides a number of biomedical applications including 1) concurrent osteogenesis, osteoinduction, osteoconduction, and bacteriostasis, such as in spinal and dental implants; 2) killing of both gram-positive and gram-negative bacteria according to different mechanisms; 3) inactivation of human and animal viruses, bacteria, and fungi; and 4) polymer- or metal-matrix composites, natural or manmade fibers, polymers, or metals containing silicon nitride powder retain key silicon nitride bone restorative, bacteriostatic, antiviral, and antifungal properties.

In an embodiment, an antiviral composition may include silicon nitride. For example, the antiviral composition may an apparatus that includes silicon nitride powder. In some embodiments, the antiviral apparatus may be a monolithic component comprising up to 100% silicon nitride. Such a component can be fully dense possessing no internal porosity, or it may be porous, having a porosity that ranges from about 1% to about 80%. The monolithic component may be used as a medical device or may be used in an apparatus in which the inactivation of a virus may be desired. In another embodiment, an antiviral composition may be incorporated within a device or in a coating to inactivate viruses on or within the device. In some embodiments, the antiviral composition may be a slurry comprising silicon nitride powder.

In some embodiments, the antiviral composition may inactivate or decrease the transmission of human viruses. Non-limiting examples of viruses that may be inactivated by the antipathogenic composition include coronaviruses (e.g. SARS-CoV-2), Influenza A, H1N1, enterovirus, and Feline calicivirus. For example, a silicon nitride composition may be effective in the inactivation of the Influenza A virus. In other examples, a silicon nitride composition may be effective in the inactivation of the SARS-CoV-2 virus.

Silicon nitride may be antipathogenic due to release of nitrogen containing species when in contact with an aqueous medium, or biologic fluids and tissues. The surface chemistry of silicon nitride may be shown as follows:

$$Si_3N_4 + 6H_2O \rightarrow 3SiO_2 + 4NH_3$$

$$SiO_2 + 2H_2O \rightarrow Si(OH)_4$$

Nitrogen elutes faster (within minutes) than silicon because surface silanols are relatively stable. For viruses, it was surprisingly found that silicon nitride may provide for RNA cleavage via alkaline transesterification which leads to loss in genome integrity and virus inactivation. This may also reduce the activity of hemagglutinin. The elution of ammonia, along with an attendant increase in pH, inactivates viruses, bacteria, and fungi. As shown in the examples, it was surprisingly found that each of silicon nitride inactivates a coronavirus and Influenza A.

In an embodiment, the antipathogenic composition may exhibit elution kinetics that show: (i) a slow but continuous elution of ammonia from the solid state rather than from the usual gas state; (ii) no damage or negative effect to mammalian cells; and (iii) an intelligent elution that increases with decreasing pH.

The use of copper (Cu), a historically-recognized viricidal agent, is limited by its cell toxicity. In contrast to Cu, ceramic devices or apparatuses made of $Si_3N_4$ are biocompatible and not toxic to the human body. An advantage of $Si_3N_4$ is the versatility of the material; thus $Si_3N_4$ may be incorporated into polymers, bioactive glasses, and even other ceramics to create composites and coatings that retain the favorable biocompatible and antiviral properties of $Si_3N_4$.

An antiviral device or apparatus may include a silicon nitride composition on at least a portion of a surface of the device for antiviral, antibacterial, or antifungal action. In an embodiment, an antiviral device may include a silicon nitride coating on at least a portion of a surface of the device. The silicon nitride coating may be applied to the surface of the device the device as a powder. In some examples, the silicon nitride powder may be filled, imbedded, or impregnated in at least a portion of the device. In some embodiments, the powder may be micrometric or nanometer in size. The average particle size may range from about 100 nm to about 5 μm, from about 300 nm to about 1.5 μm, or from about 0.6 μm to about 1.0 μm. In other embodiments, the silicon nitride may be incorporated into the device. For example, a device may incorporate silicon nitride powder within the body of the device. In one embodiment, the device may be made of silicon nitride. In another embodiment, the composition can comprise a slurry or suspension of nitride particles.

The silicon nitride coating may be present on the surface of an apparatus or within the apparatus in a concentration of about 1 wt. % to about 100 wt %. In various embodiments, the coating may include about 1 wt. %, 2 wt. %, 5 wt. %, 7.5 wt. %, 8.3 wt. %, 10 wt. %, 15 wt. %, 16.7 wt. %, 20 wt. %, 25 wt. %, 30 wt. %, 33.3 wt. %, 35 wt. %, or 40 wt. % silicon nitride powder. In some examples, the coating may include about 10 wt. % to about 20 wt. % silicon nitride. In at least one example, the coating includes about 15 wt. % silicon nitride. In some embodiments, silicon nitride may be embedded in (as a filler) or on the surface of a device or apparatus in a concentration of about 1 wt. % to about 100 wt. %. In various embodiments, a device or apparatus may include about 1 wt. %, 2 wt. %, 5 wt. %, 7.5 wt. %, 8.3 wt. %, 10 wt. %, 15 wt. %, 16.7 wt. %, 20 wt. %, 25 wt. %, 30 wt. %, 33.3 wt. %, 35 wt. %, 40 wt. %, 50 wt. %, 60 wt. %, 70 wt. %, 80 wt. %, 90 wt. %, to 100 wt. % silicon nitride. In some examples, the silicon nitride may be on the surface of the apparatus at a concentration of about 10 wt. % to about 20 wt. %. In at least one example, the silicon nitride may be on the surface of the apparatus at a concentration of about 15 wt. % silicon nitride.

In some embodiments, the antiviral composition may be a monolithic component consisting of the silicon nitride. Such a component can be fully dense possessing no internal porosity, or it may be porous, having a porosity that ranges from about 1% to about 80%. The monolithic component may be used as a medical device or may be used in an apparatus in which the inactivation of a virus may be desired.

In various embodiments, a device or apparatus that includes silicon nitride for antiviral properties may be a medical device. Non-limiting examples of medical devices or apparatuses include orthopedic implants, spinal implants, pedicle screws, dental implants, in-dwelling catheters, endotracheal tubes, colonoscopy scopes, and other similar devices.

In some embodiments, silicon nitride may be incorporated within or applied as a coating to materials or apparatuses for antiviral properties such as polymers and fabrics, surgical gowns, tubing, clothing, air filters and water filters, masks, tables such as hospital exam and surgical tables, desks, fixtures, handles, knobs, toys, and filters such as air conditioner filters, or toothbrushes. In some examples, the filters may be within filtration devices of anesthesia machines, ventilators, or CPAP machines such that an antimicrobial surface layer in the filter can trap pulmonary pathogens, as air moves in and out of infected lungs.

In other embodiments, silicon nitride powder may be incorporated into compositions including, but not limited to slurries, suspensions, gels, sprays, paint, or toothpaste. For example, the addition of silicon nitride to a slurry, such as paint, that is then applied to a surface may provide an antibacterial, antifungal, and antiviral surface. In other embodiments, silicon nitride may be mixed with water along with any appropriate dispersants and slurry stabilization agents, and thereafter applied by spraying the slurry onto various surfaces. An example dispersant is Dolapix A88.

In some embodiments, silicon nitride may be included in an antiviral composition at a concentration of about 5 wt. % to about 20 wt. %. In at least one example, the composition may include about 15 wt. % silicon nitride. Alternatively, in some embodiments, silicon nitride may be included in an antiviral composition at a concentration of about 5 wt. % to about 20 wt. %. In at least one example, the composition may include about 15 wt. % silicon nitride. In an example, the antiviral composition may be a slurry of silicon nitride powder and water. Silicon nitride may be combined with water to form an aqueous slurry at concentrations of about 0.1 wt. % up to about 70 wt. %. In some embodiments, the silicon nitride powder may be present in the slurry in a concentration of about 0.1 wt. % to about 55 wt. %. In other embodiments, silicon nitride may be incorporated within organic suspensions, gels, sprays, and/or paints at concentrations of about 0.1 wt. % up to about 70 wt. % or about 0.1 wt. % up to about 55 wt. %. In various embodiments, the slurry, organic suspension, gel, spray, and/or paint may include about 0.1 wt. %, 0.5 wt. %, 1 wt. %, 1.5 wt. %, 2 wt. %, 5 wt. %, 10 wt. %, 15 wt. %, 20 wt. %, 25 wt. %, 30 wt. %, 35 wt. %, 40 wt. %, 45 wt. %, 50 wt. %, or 55 wt. % silicon nitride.

In some embodiments, the composition comprises a toothpaste and the silicon nitride is in the form of a powder that is directly substituted for silicon dioxide powder found in standard toothpaste. The silicon nitride powder may be substituted for silicon dioxide powder in toothpaste at concentrations of about 1 wt. % to about 30 wt. %. In some examples, silicon nitride may be present within a toothpaste at a concentration of about 1 wt. %, 5 wt. %, 10 wt. %, 15 wt. %, 20 wt. %, The silicon nitride not only serves to be an antiviral and antibacterial agent in the toothpaste, but it also may serve as a polishing agent similar to silicon dioxide.

Further provided herein is a method of inactivating a pathogen by contacting a virus with an antiviral composition comprising silicon nitride. In an embodiment, the method may include coating a device or apparatus with silicon nitride and contacting the coated apparatus with the virus. Coating the apparatus may include applying a silicon nitride powder to a surface of the apparatus. In other embodiments, the silicon nitride powder may be filled, incorporated, or impregnated within the device or apparatus.

Without being limited to a particular theory, the antiviral composition may decrease viral action by alkaline transesterification and reduce the activity of hemagglutinin. It was surprisingly found that silicon nitride powder (i) remarkably decreases viral action by alkaline transesterification through the breakage of RNA internucleotide linkages and (ii) markedly reduced the activity of hemagglutinin thus disrupting host cell recognition by denaturing protein structures on viral surfaces leading to the inactivation of viruses regardless of the presence of a viral envelope.

In an embodiment, the antipathogenic composition may exhibit elution kinetics that show: (i) a slow but continuous elution of ammonia from the solid state rather than from the usual gas state; (ii) no damage or negative effect to mammalian cells; and (iii) an intelligent elution which increases with decreasing pH. Moreover, the inorganic nature of silicon nitride may be more beneficial than the use of petrochemical or organometallic bactericides, virucides, and fungicides which are known to harm mammalian cells or have residual effects in soil, on plants, and in vegetables or fruit.

Also provided herein is a method of treating or preventing a pathogen at a location in a human patient. For example, the pathogen may be a virus. The method may include contacting the patient with a device, apparatus, or composition comprising silicon nitride. Without being limited to any one theory, the silicon nitride inactivates the virus (for example, a coronavirus, such as SARS-CoV-2, or Influenza A). The device, apparatus, or composition may include about 1 wt. % to about 100 wt. % silicon nitride. In some examples, the device or apparatus may include about 1 wt. % to about 100 wt. % silicon nitride on the surface of the device or apparatus. In an embodiment, the device or apparatus may be a monolithic silicon nitride ceramic. In another embodiment, the device or apparatus may include a silicon nitride coating, such as a silicon nitride powder coating. In another embodiment, the device or apparatus may incorporate silicon nitride into the body of the device. For example, silicon nitride powder may be incorporated or impregnated into the body of the device or apparatus using methods known in the art.

In some embodiments, the composition or apparatus may be contacted with the patient or user for at least 1 minute, at least 5 minutes, at least 30 minutes, at least 1 hour, at least 2 hours, at least 5 hours, or at least 1 day. In at least one example, the device or apparatus may be permanently implanted in the patient. In at least one example, the device or apparatus may be worn externally by a user. In another example, the apparatus may be a high contact surface. In further examples, the apparatus may be in continuous or sustained contact with a body fluid of a patient. The body fluid may be blood or gas (inhalation or exhalation gas).

In some embodiments, the virus is at least 70% inactivated, at least 75% inactivated, at least 80% inactivated, at least 85% inactivated, at least 90% inactivated, at least 95% inactivated, or at least 99% inactivated after contact with the silicon nitride in the composition or apparatus for at least 1 minute, at least 5 minutes, or at least 30 minutes. In at least one example, the virus is at least 85% inactivated after contact with the silicon nitride in the composition or apparatus for at least 1 minute. In another example, the virus is at least 99% inactivated after contact with the silicon nitride in the composition or apparatus for at least 30 minutes.

EXAMPLES

Example 1: Effect of Silicon Nitride Concentration on Virus Inactivation

Figure 2A:
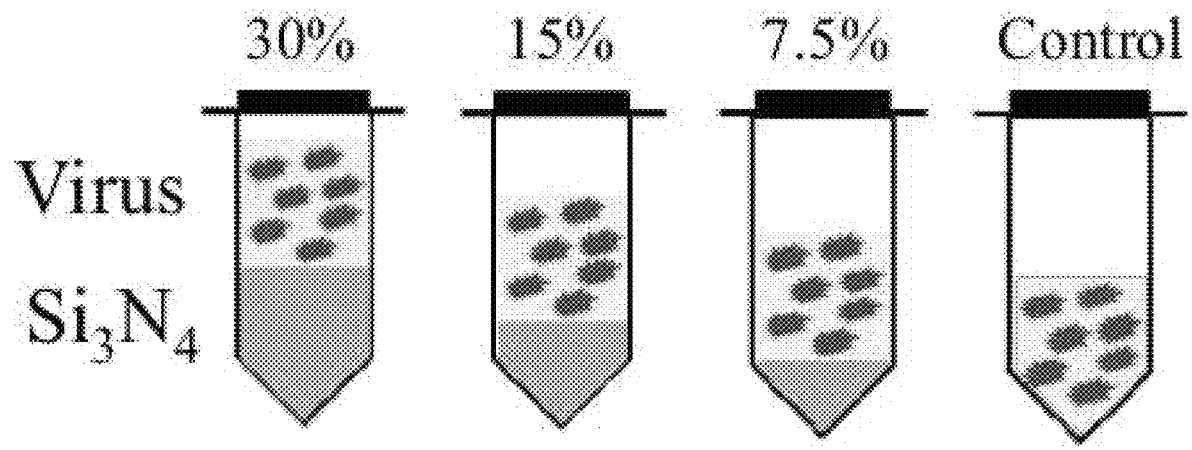
FIG. 2A is an illustration of a virus exposed to 0 wt. %, 7.5 wt. %, 15 wt. %, and 30 wt. % $Si_3N_4$ for 10 minutes.

To show the effect of silicon nitride concentration on the inactivation of viruses, Influenza A was exposed to various concentrations of $Si_3N_4$ powder. To prepare the silicon nitride, a specific weight of silicon nitride powder mixed with pure distilled water. For instance, 7.5 g of silicon nitride was dispersed in 92.5 g of pure distilled water. The virus was added to this mixture in concentrations of 1:1, 1:10 and 1:100 virus/mixture, respectively. These mixtures were then allowed to incubate under gentle agitation for 10 minutes at 4° C. Influenza A was exposed to 0 wt. %, 7.5 wt. %, 15 wt. %, and 30 wt. % $Si_3N_4$ for 10 minutes at 4° C., as illustrated in FIG. 2A. The mixtures were then filtered to remove the silicon nitride powder.

Figure 2B:
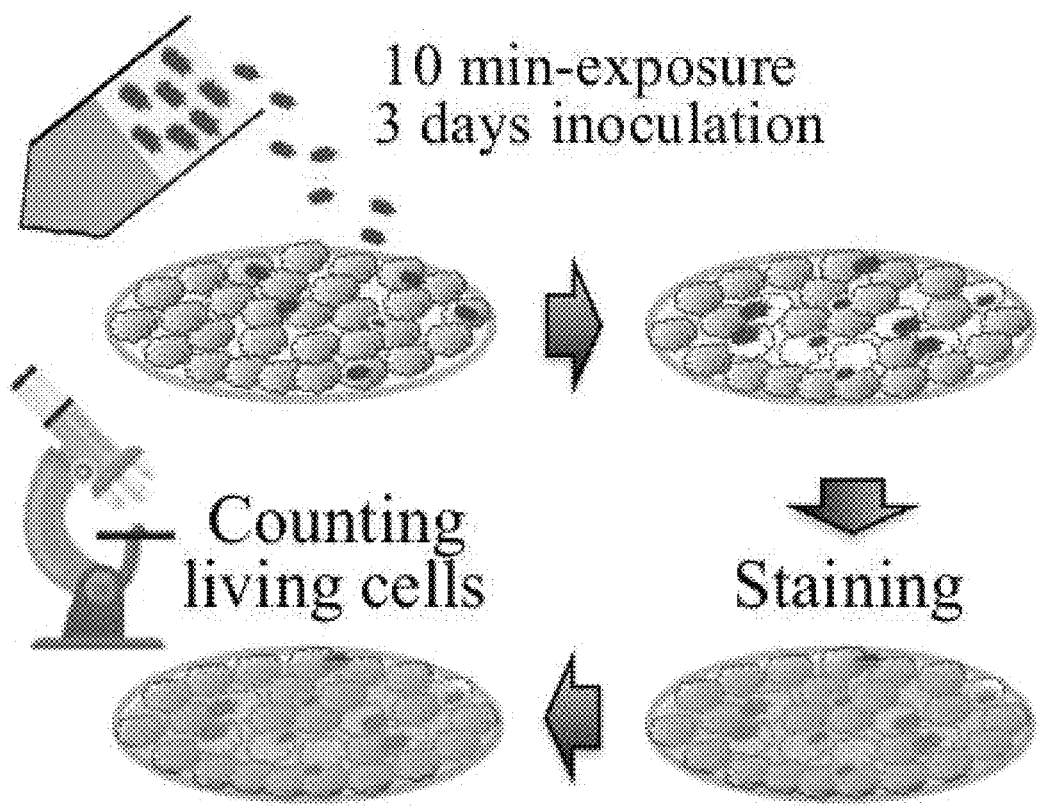
FIG. 2B is an illustration of methods used to determine viability of cells inoculated with a virus exposed to $Si_3N_4$ according to FIG. 2A.

Influenza A virus-inoculated Madin-Darby canine kidney (MDCK) cells were then observed for the effectiveness of $Si_3N_4$ in inactivating the Influenza A. The remaining mixtures were then inoculated into Petri dishes containing living MDCK cells within a biogenic medium. The amount of living MDCK cells were subsequently counted using staining methods after 3 days exposure. The viability of MDCK cells was determined after inoculating the cells for 3 days with Influenza A exposed to $Si_3N_4$ according to FIG. 2B.

Figure 4A:
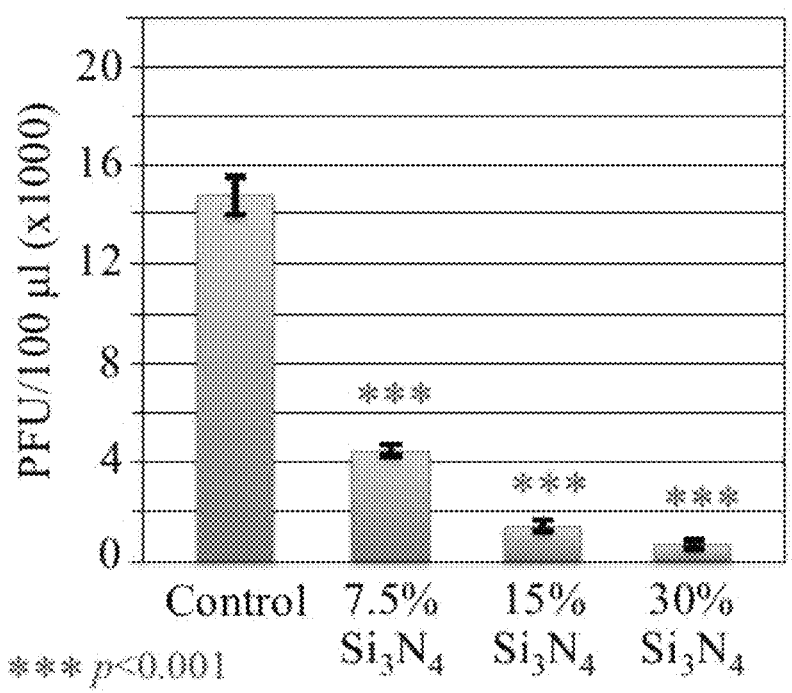
FIG. 4A is a graph of PFU/100 µl for Influenza A exposed to 0 wt. %, 7.5 wt. %, 15 wt. %, and 30 wt. % $Si_3N_4$ for 10 minutes according to FIG. 2A.
Figure 4B:
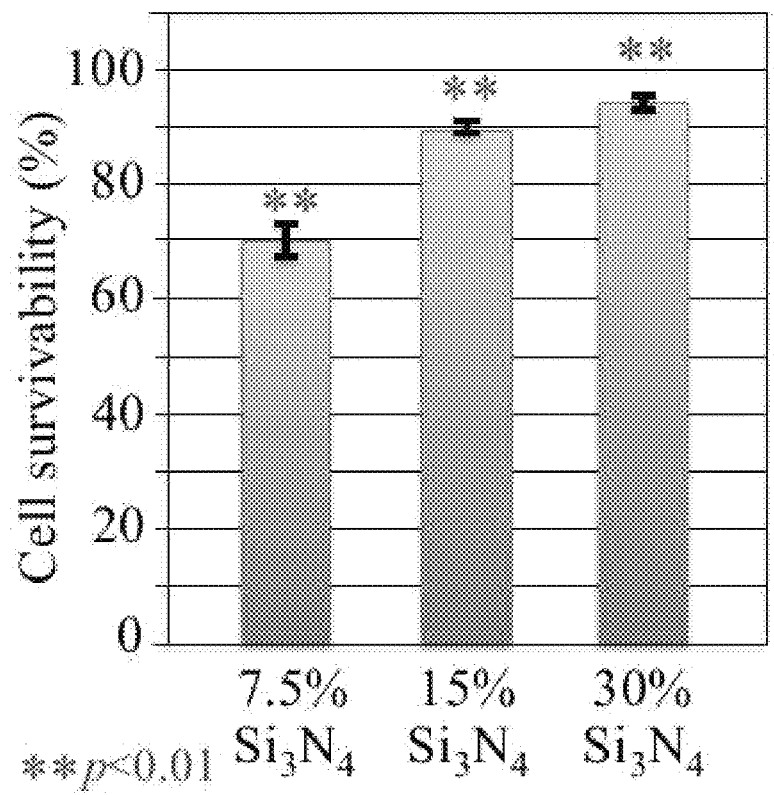
FIG. 4B is a graph of cell survivability of cells inoculated with Influenza A exposed to 7.5 wt. %, 15 wt. %, and 30 wt. % $Si_3N_4$ for 10 minutes according to FIG. 2B.
Figure 5:
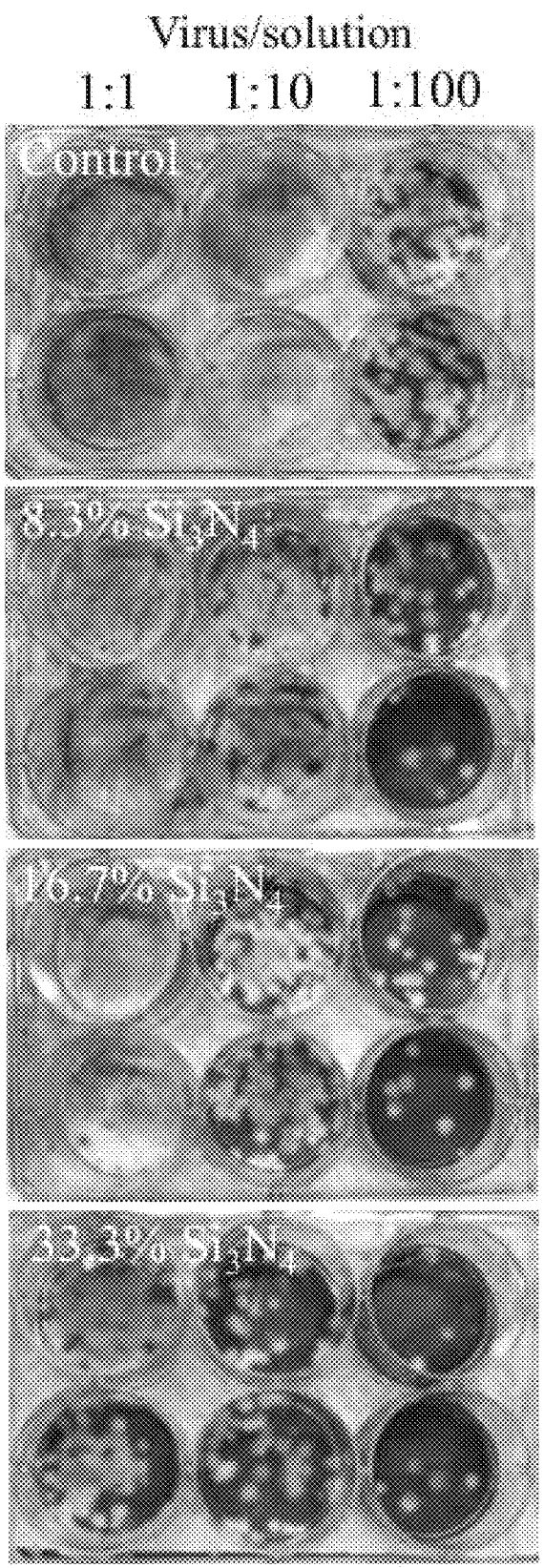
FIG. 5 includes photographs of cells inoculated with different ratios of virus to slurry that had been exposed to various concentrations of $Si_3N_4$.
Figures 6A, 6B, 6C:
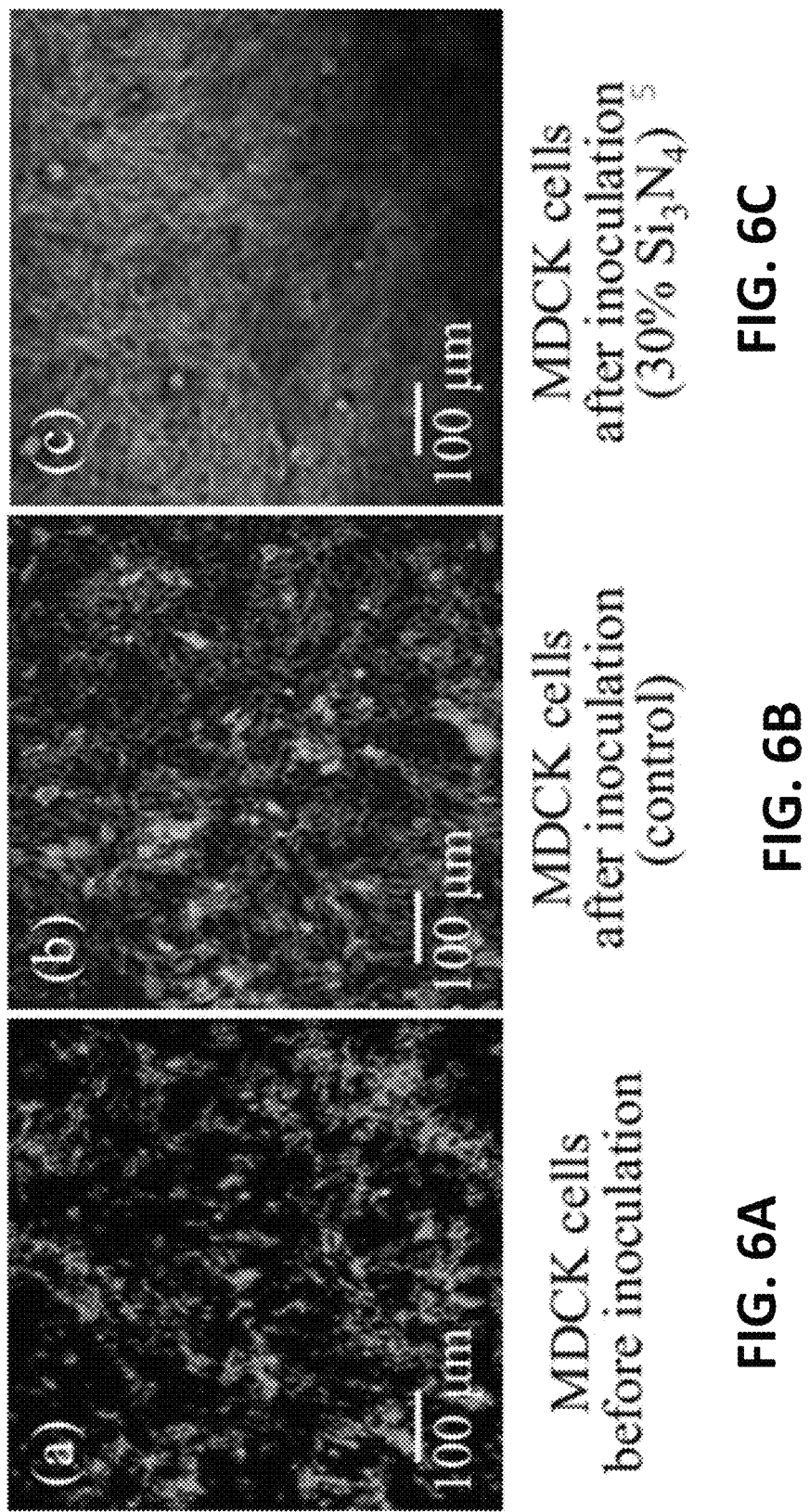
FIG. 6A shows a fluorescence microscopy image of MDCK cells before inoculation.
FIG. 6B shows a fluorescence microscopy image of MDCK cells after inoculation with a virus exposed to the control.
FIG. 6C shows a fluorescence microscopy image of MDCK cells after inoculation with a virus exposed to 30 wt. % $Si_3N_4$.

FIG. 4A is a graph of PFU/100 μl for Influenza A exposed to 0 wt. %, 7.5 wt. %, 15 wt. %, and 30 wt. % $Si_3N_4$ for 10 minutes. FIG. 4B is a graph of cell survivability of cells inoculated with Influenza A exposed to 7.5 wt. %, 15 wt. %, and 30 wt. % $Si_3N_4$ for 10 minutes.

Example 2: Effect of Exposure Time and Temperature on Virus Inactivation

Figure 3A:
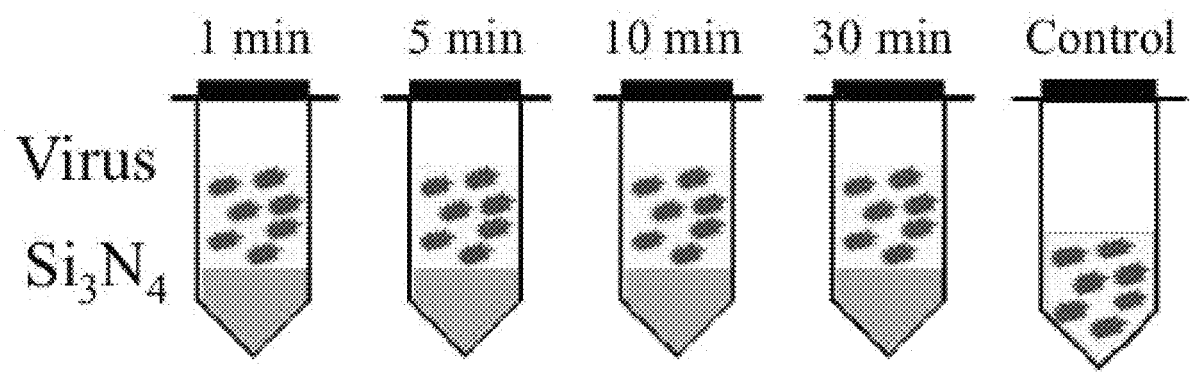
FIG. 3A is an illustration of a virus exposed to 15 wt. % $Si_3N_4$ for 1, 5, 10, and 30 minutes.
Figure 3B:
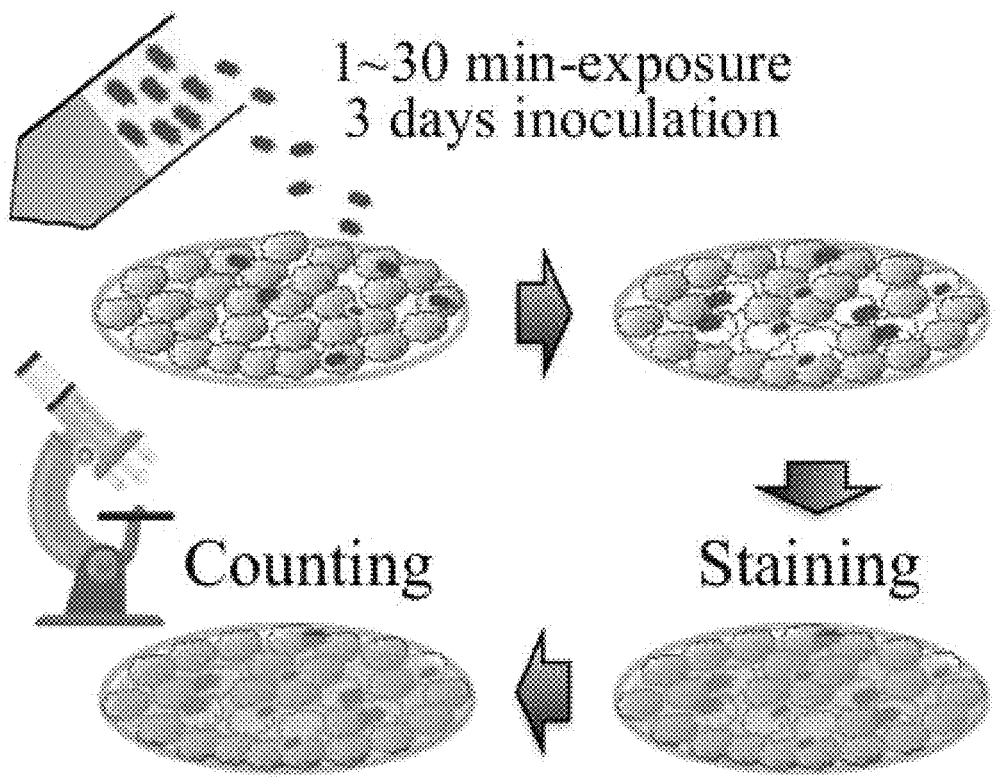
FIG. 3B is an illustration of methods used to determine viability of a virus after exposure to $Si_3N_4$ according to FIG. 3A.

To show the effect of silicon nitride on the inactivation of viruses, Influenza A was exposed to a fixed concentration of $Si_3N_4$ powder (15 wt. %) for various times and temperatures. The mixture was then allowed to incubate under gentle agitation for 1-30 minutes at room temperature and at 4° C. For example, Influenza A was exposed to 15 wt. % $Si_3N_4$ for 1, 5, 10, or 30 minutes at room temperature or 4° C., as illustrated in FIG. 3A. Influenza A virus-inoculated Madin-Darby canine kidney (MDCK) cells were then observed for the effectiveness of $Si_3N_4$ in inactivating the Influenza A. The viability of MDCK cells was determined after inoculating the cells for 3 days with Influenza A exposed to $Si_3N_4$ according to FIG. 3B.

Figure 7A:
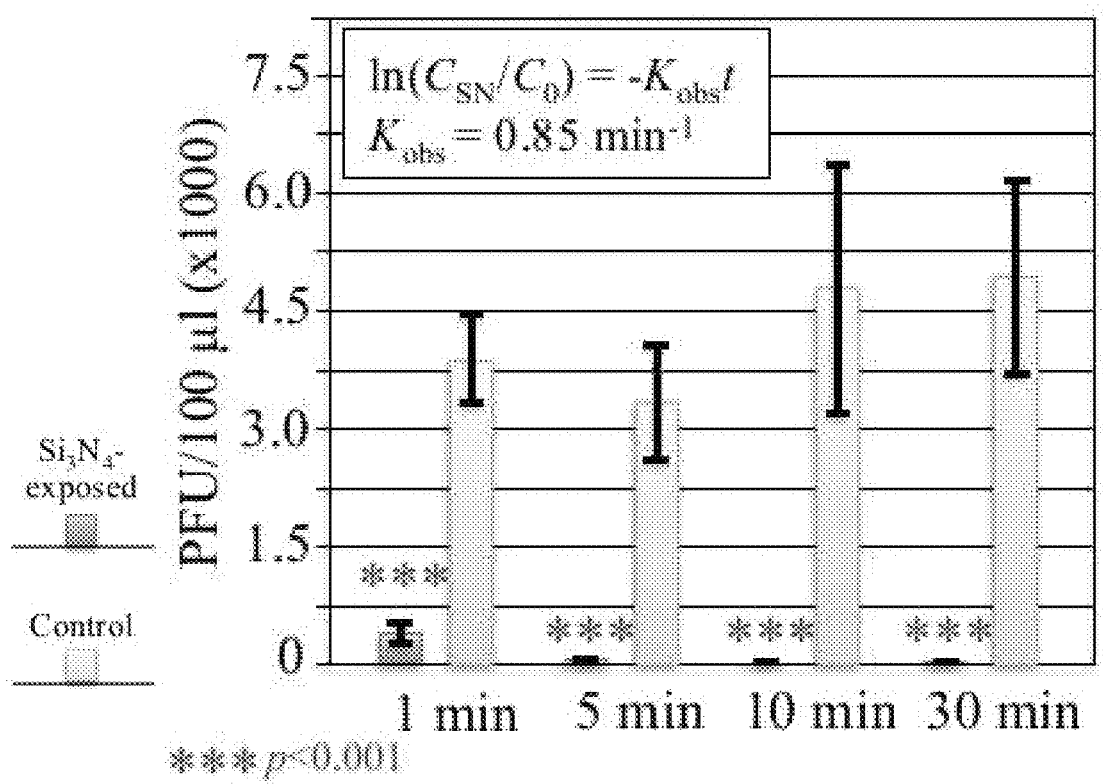
FIG. 7A is a graph of PFU/100 µl for Influenza A exposed to 15 wt. % $Si_3N_4$ for 1 minute, 5 minutes, 10 minutes, or 30 minutes at room temperature.
Figure 7B:
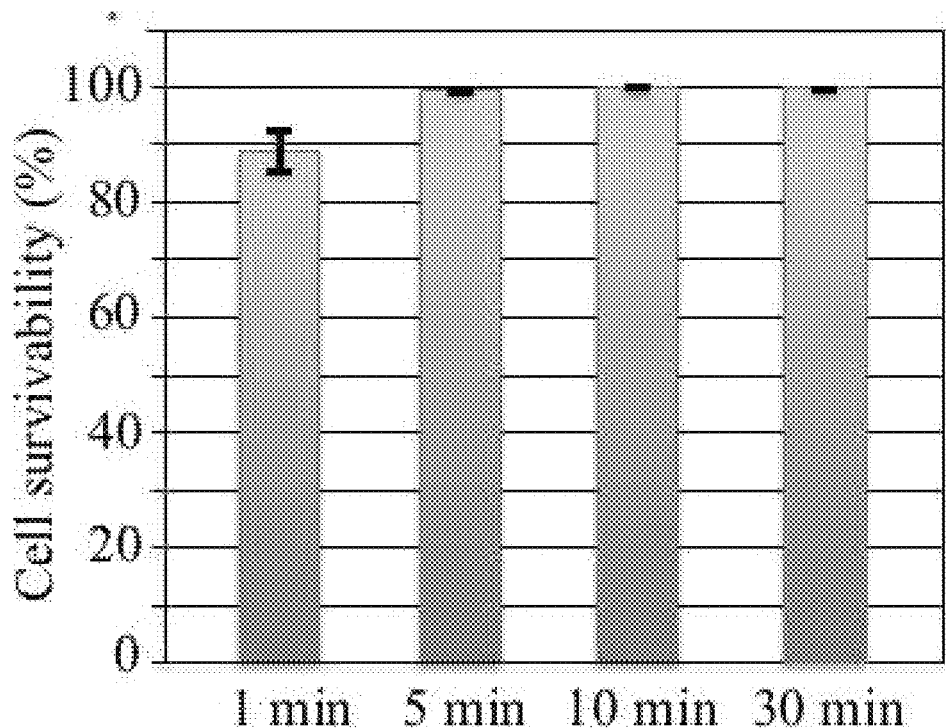
FIG. 7B is a graph of cell survivability of cells inoculated with Influenza A exposed to 15 wt. % $Si_3N_4$ for 1 minute, 5 minutes, 10 minutes, or 30 minutes at room temperature.

FIG. 7A is a graph of PFU/100 μl for Influenza A exposed to 15 wt. % $Si_3N_4$ for 1 minute, 5 minutes, 10 minutes, or 30 minutes at room temperature. FIG. 7B is a graph of cell survivability of MDCK cells inoculated with Influenza A exposed to 15 wt. % $Si_3N_4$ for 1 minute, 5 minutes, 10 minutes, or 30 minutes at room temperature.

Figure 8A:
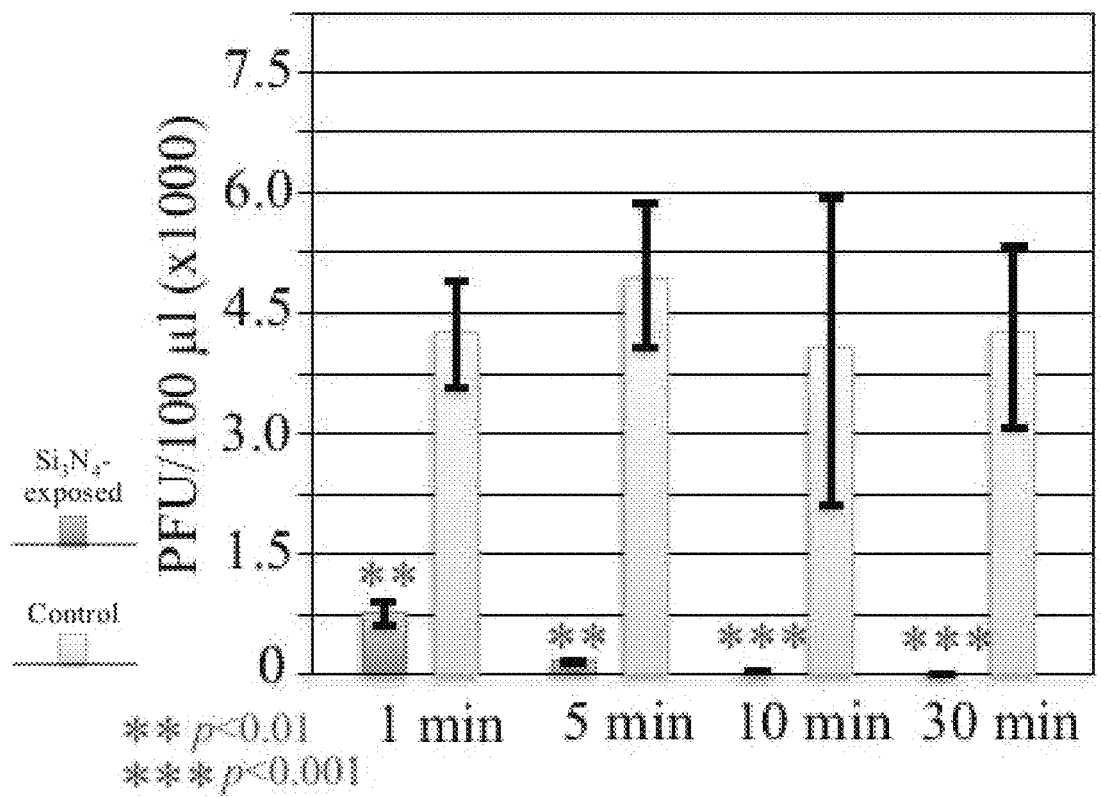
FIG. 8A is a graph of PFU/100 µl for Influenza A exposed to 15 wt. % $Si_3N_4$ for 1 minute, 5 minutes, 10 minutes, or 30 minutes at 4° C.
Figure 8B:
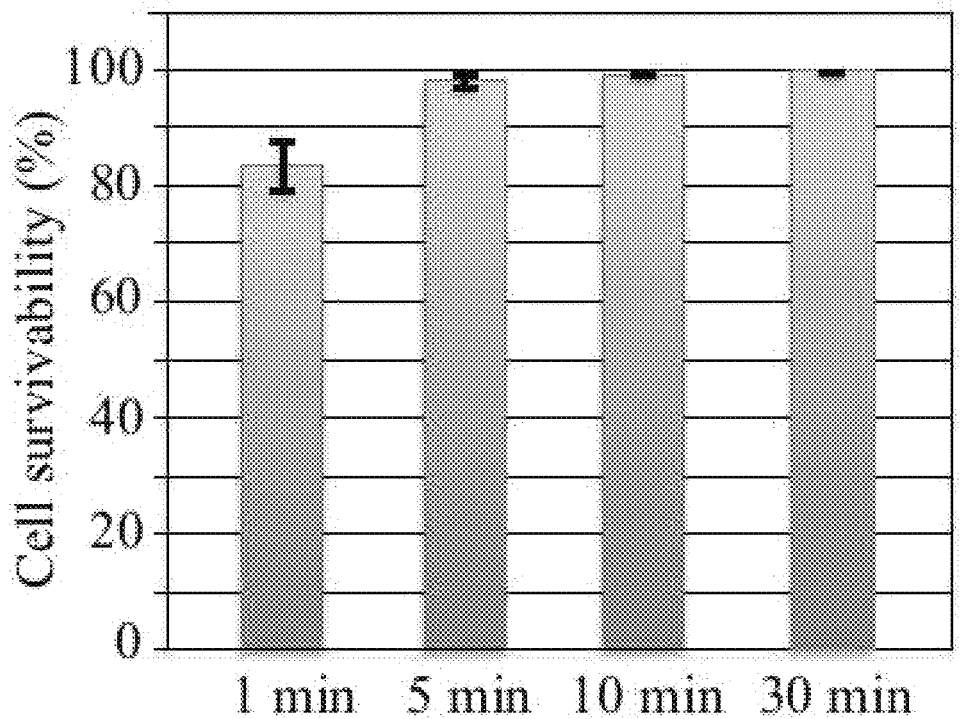
FIG. 8B is a graph of cell survivability of cells inoculated with Influenza A exposed to 15 wt. % $Si_3N_4$ for 1 minute, 5 minutes, 10 minutes, or 30 minutes at 4° C.
Figures 9A, 9B:
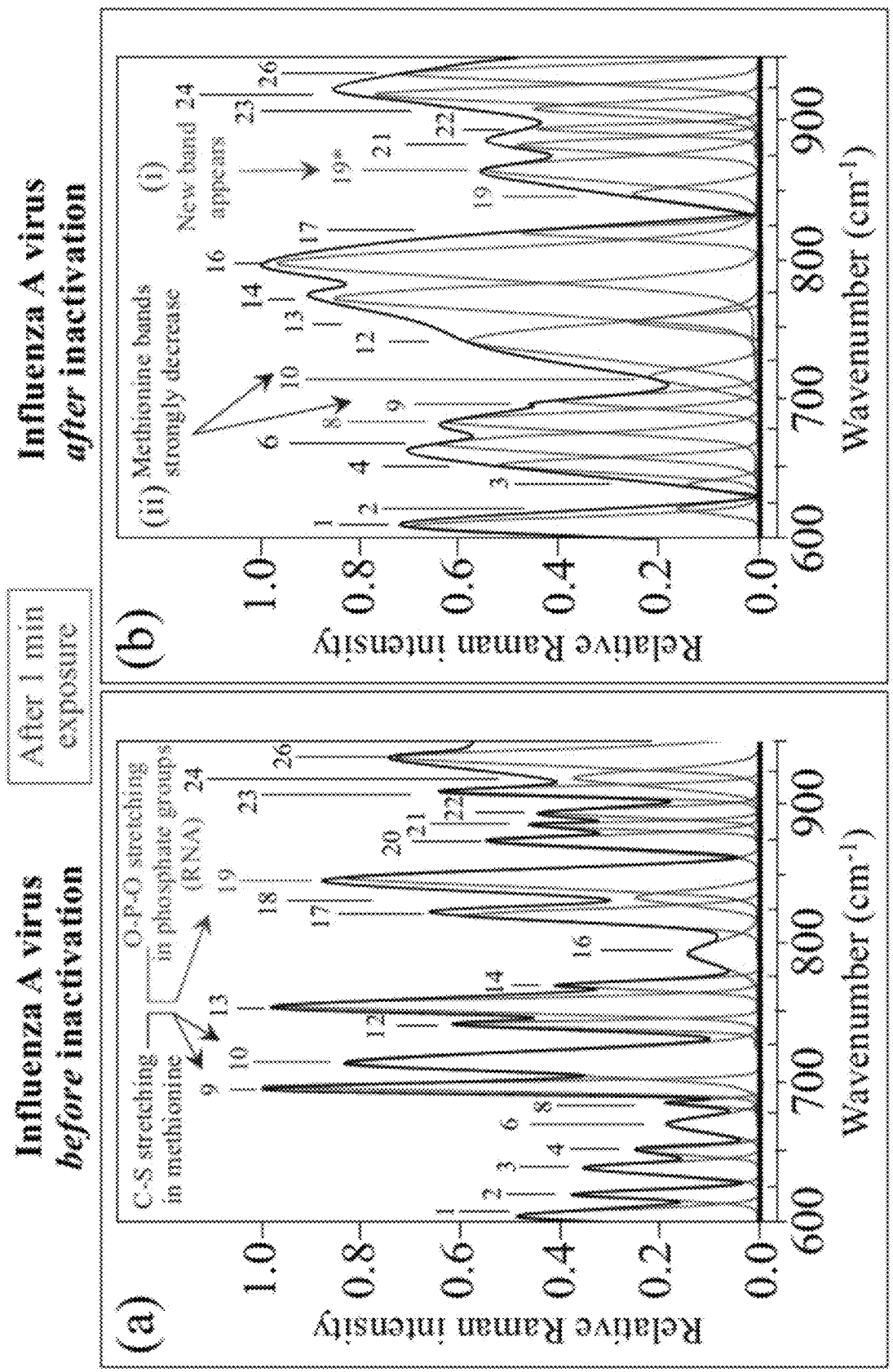
FIG. 9A shows the Raman spectrum of Influenza A virus before inactivation.
FIG. 9B shows changes in the Raman spectrum of the Influenza A virus relevant to chemical modifications in RNA and hemagglutinin after inactivation after 1 minute of exposure.
Figure 11:
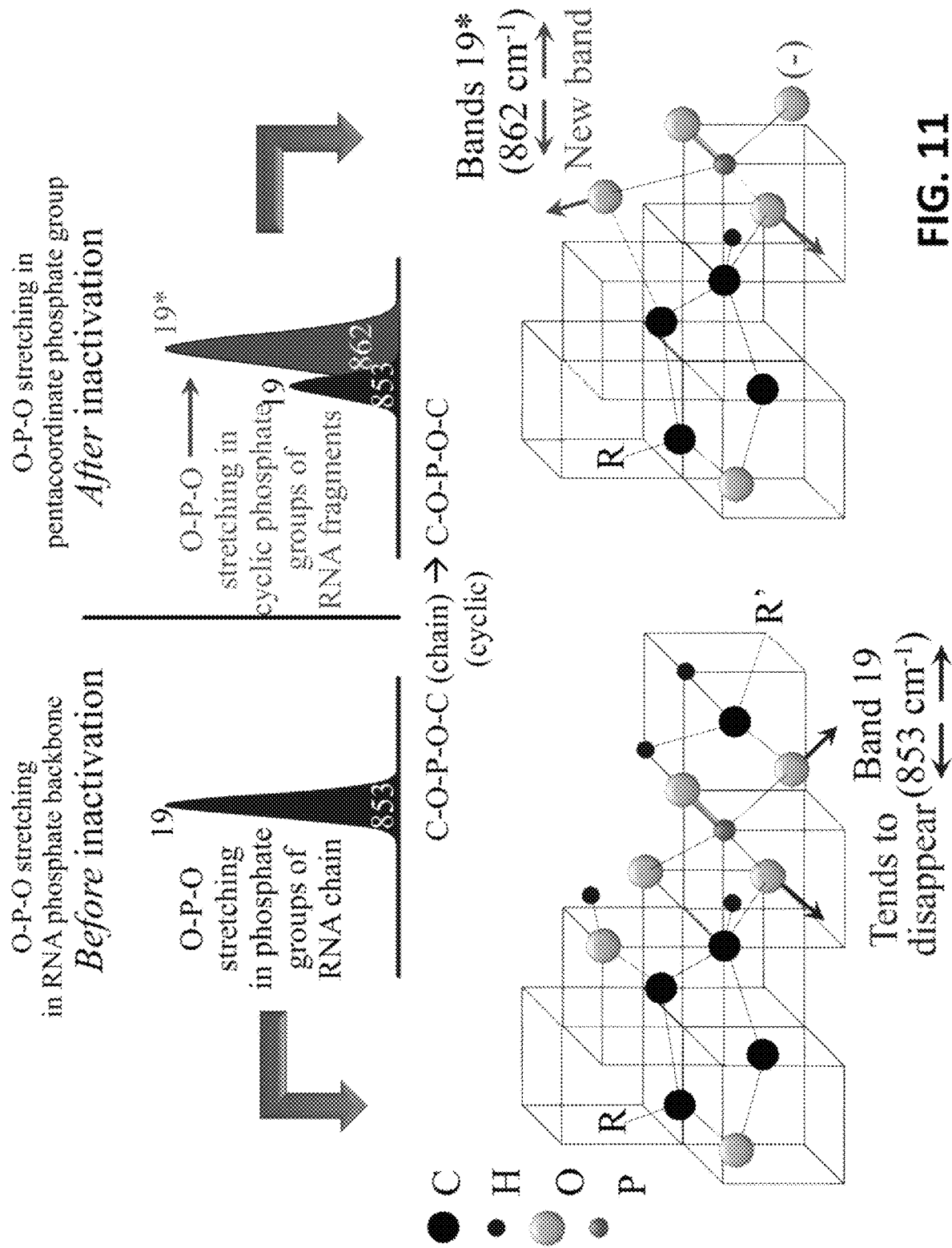
FIG. 11 shows O—P—O stretching in pentacoordinate phosphate group after inactivation.
Figure 12B:
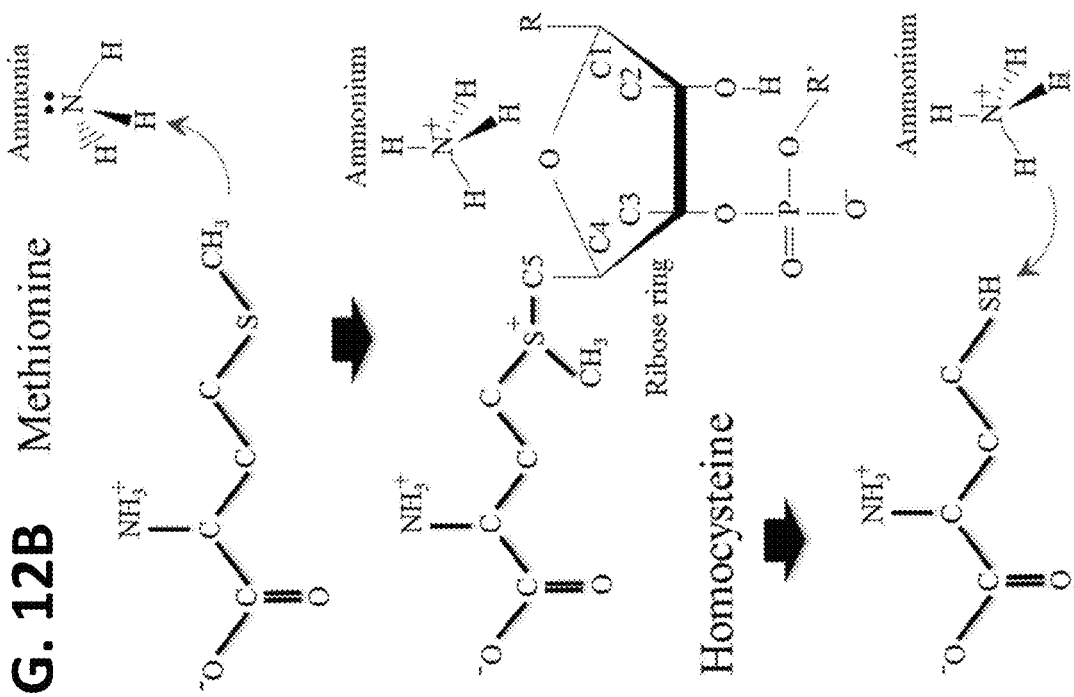
FIG. 12B shows methionine's structural change in the presence of ammonia.
Figure 12A:
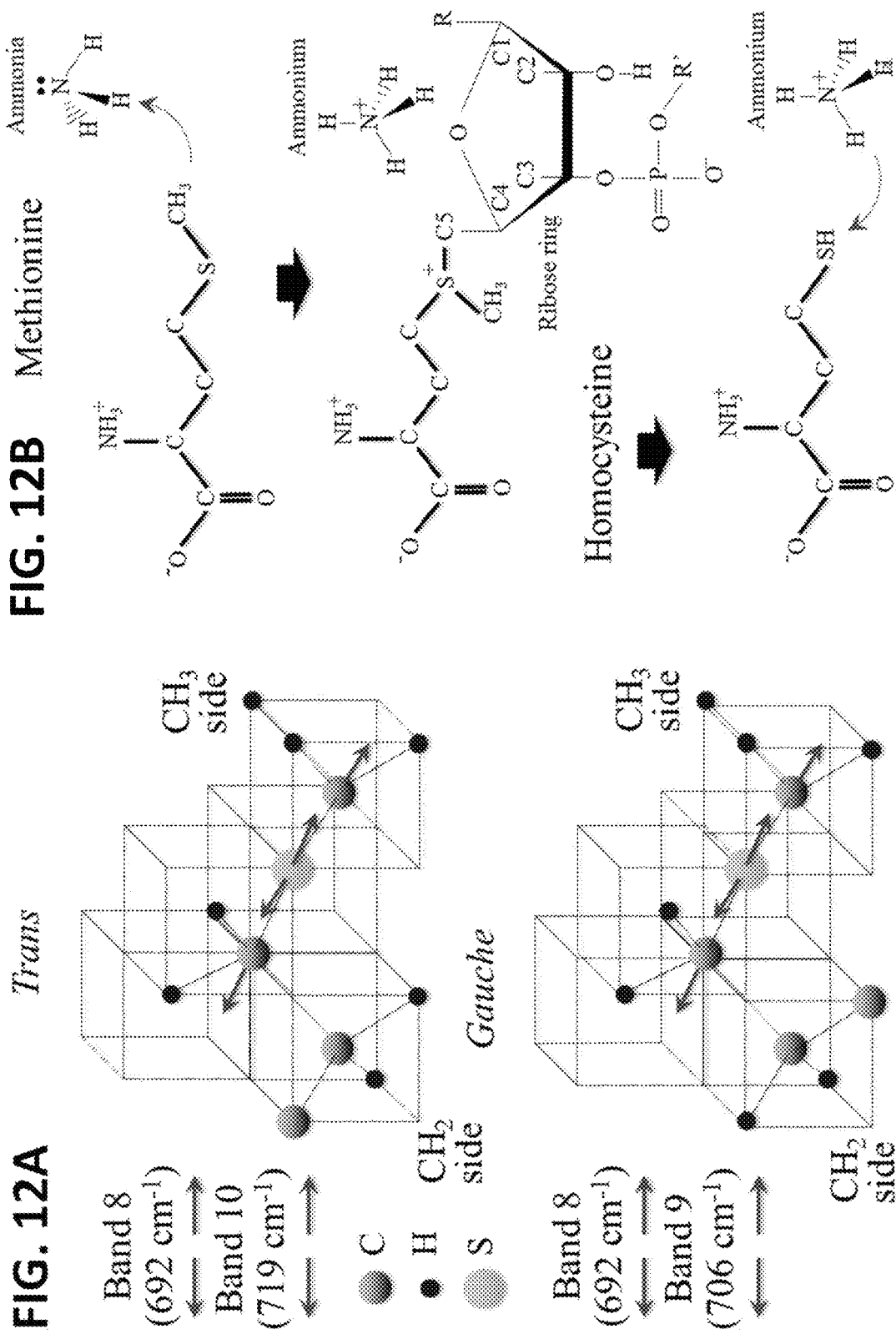
FIG. 12A shows vibrational modes of methionine in the hemagglutinin structure.
Figure 13:
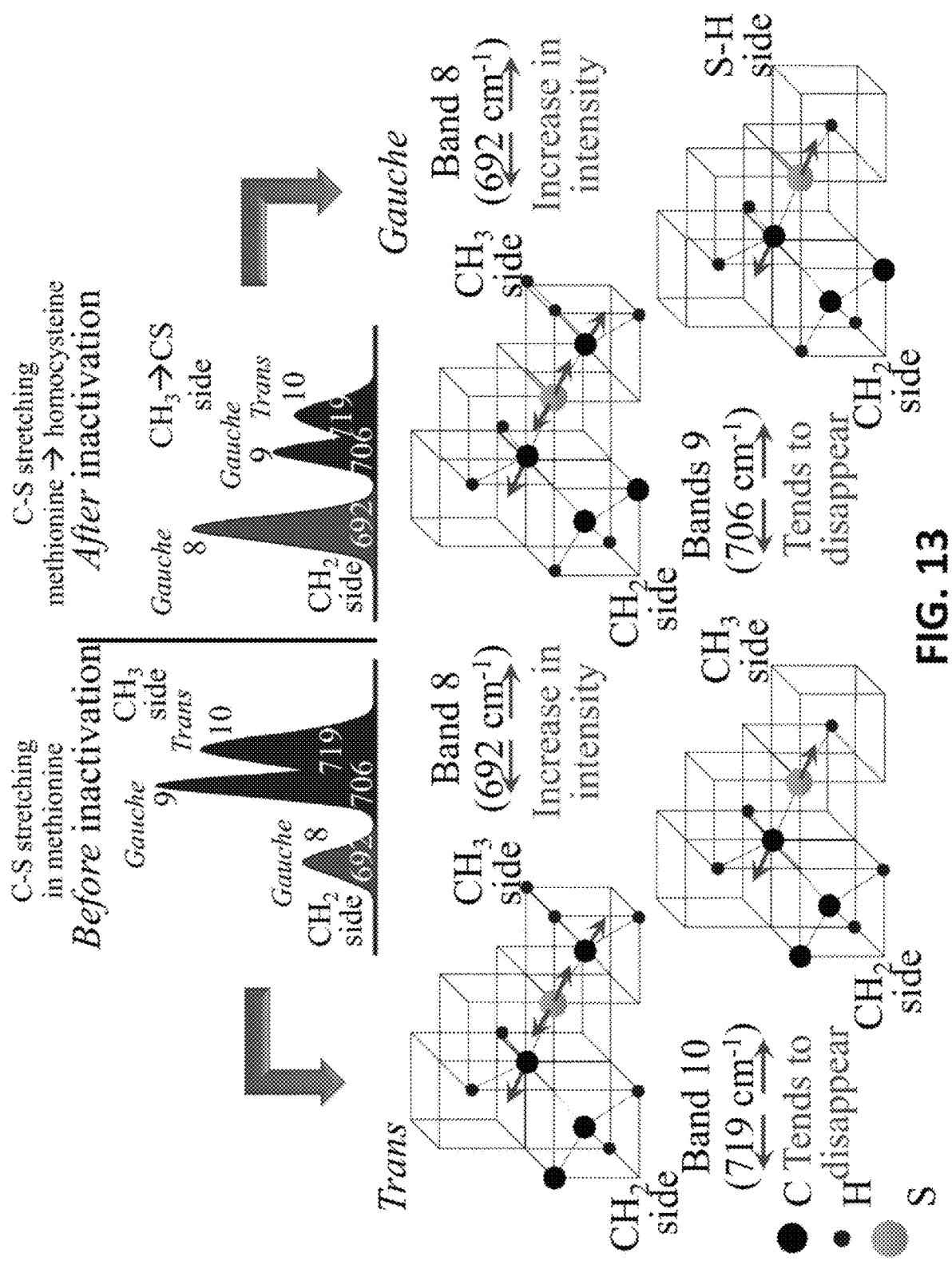
FIG. 13 shows C—S stretching methionine to homocysteine after inactivation.
Figure 14A:
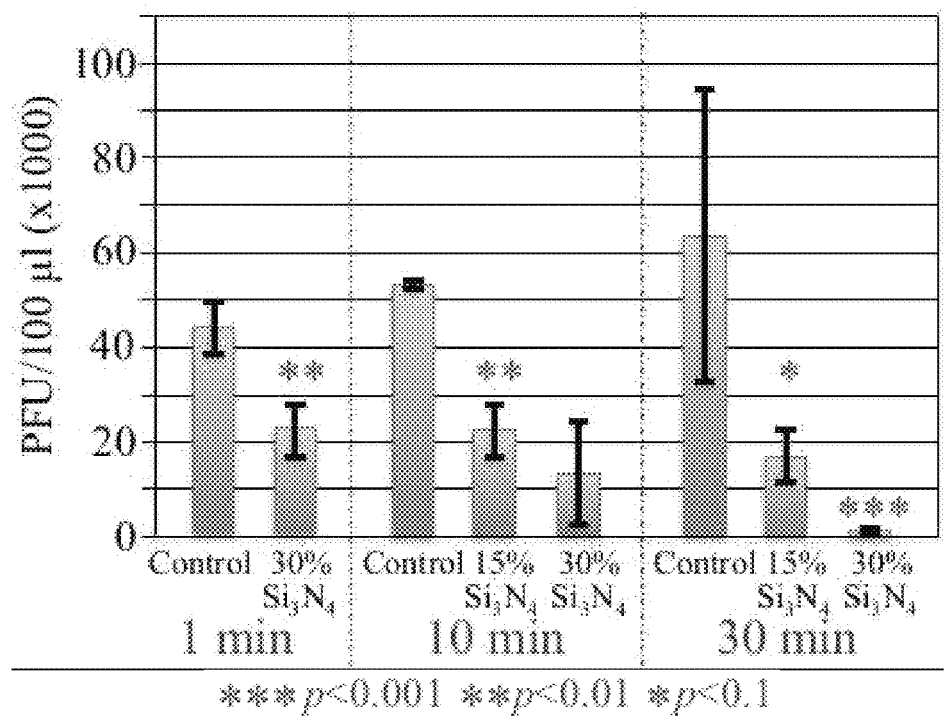
FIG. 14A is a graph of PFU/100 µl for Feline calicivirus exposed to 15 wt. % or 30 wt. % $Si_3N_4$ for 1 minute, 10 minutes, or 30 minutes.
Figure 14B:
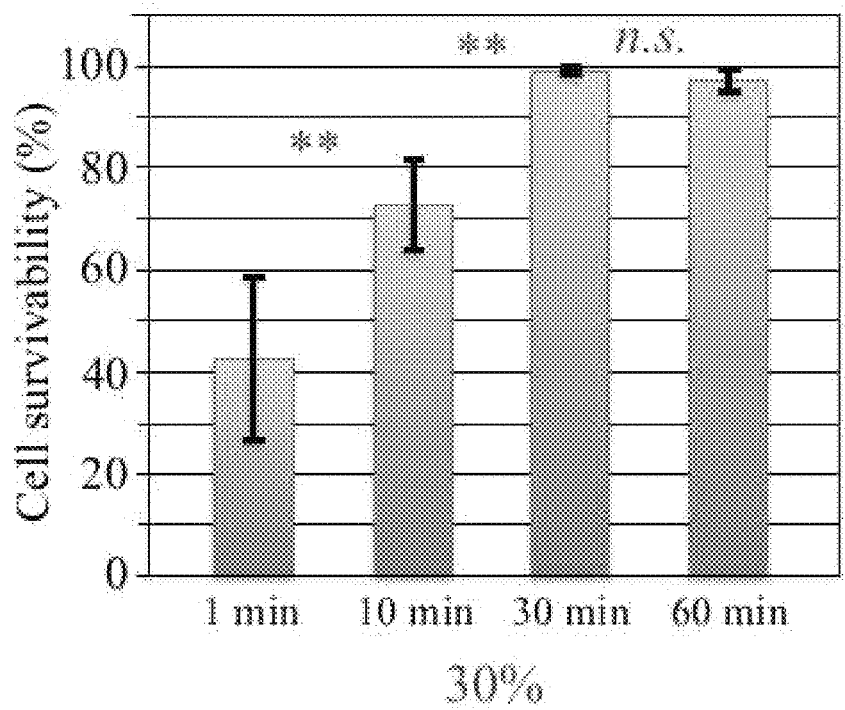
FIG. 14B is a graph of cell survivability of cells inoculated with Feline calicivirus exposed to 30 wt. % $Si_3N_4$ for 1 minute, 10 minutes, 30 minutes, or 60 minutes.

FIG. 8A is a graph of PFU/100 μl for Influenza A exposed to 15 wt. % $Si_3N_4$ for 1 minute, 5 minutes, 10 minutes, or 30 minutes at 4° C. FIG. 8B is a graph of MDCK cell survivability inoculated with Influenza A exposed to 15 wt. % $Si_3N_4$ for 1 minute, 5 minutes, 10 minutes, or 30 minutes at 4° C.

Example 3: Effect of Silicon Nitride on H1H1 Influenza a Inactivation

To show the effect of silicon nitride on the inactivation of viruses, Influenza A was exposed to a slurry of 15 wt. % silicon nitride for 10 minutes.

Figure 15A:
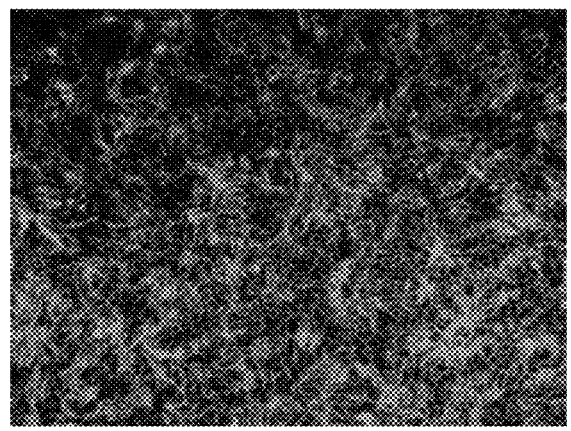
FIG. 15A shows the H1H1 Influenza A virus (nucleoprotein, NP) stained red after 10 minutes of exposure to a slurry of 15 wt. % silicon nitride and after its inoculation into a biogenic medium containing MDCK cells stained green for the presence of filamentous actin (F-actin) proteins.
Figure 15B:
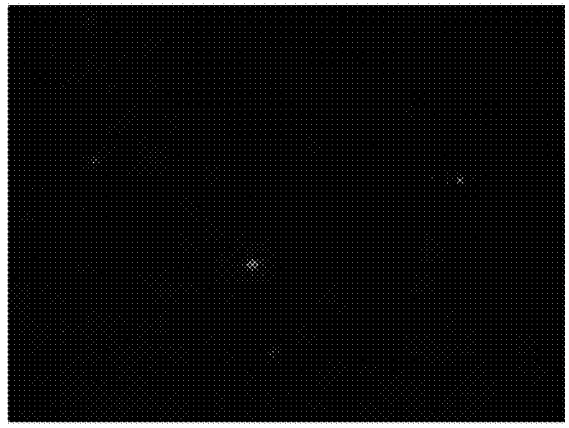
FIG. 15B shows the NP stained H1H1 Influenza A virus from FIG. 15A.
Figure 15C:
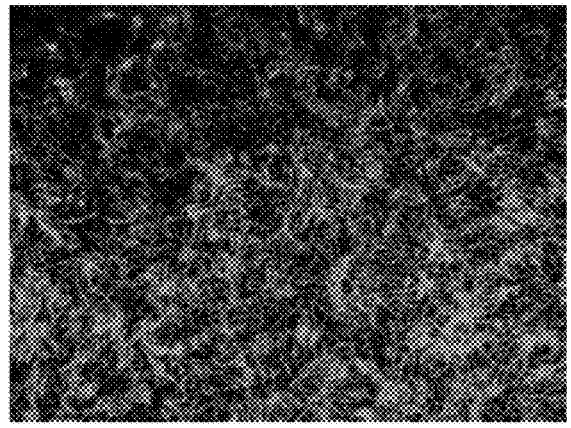
FIG. 15C shows the F-actin stained MDCK cells from FIG. 15A.
Figure 16A:
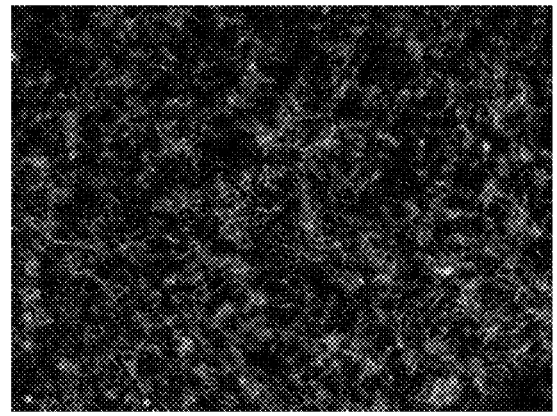
FIG. 16A shows the H1H1 Influenza A virus (nucleoprotein, NP) stained red without exposure to silicon nitride and after its inoculation into a biogenic medium containing MDCK cells stained green for the presence of filamentous actin (F-actin) proteins.
Figure 16B:
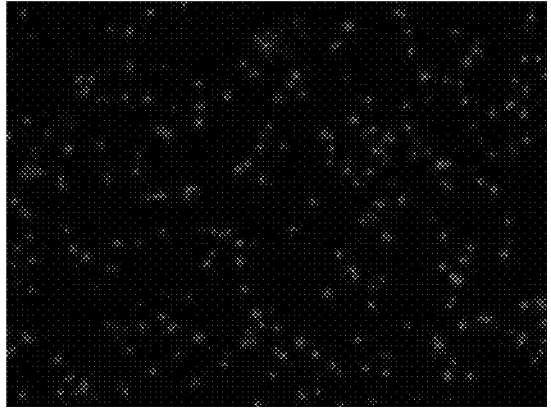
FIG. 16B shows the NP stained H1H1 Influenza A virus from FIG. 16A.
Figure 16C:
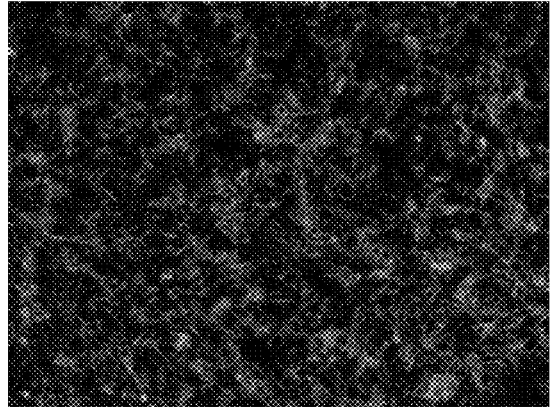
FIG. 16C shows the F-actin stained MDCK cells from FIG. 16A.

FIGS. 15A-15C show the H1H1 Influenza A virus (A/Puerto Rico/8/1934 H1N1 (PR8)) stained red (nucleoprotein, NP) after its inoculation into a biogenic medium containing MDCK cells stained green for the presence of filamentous actin (F-actin) proteins which are found in all eukaryotic cells. FIGS. 16A-16C shows the effect of the virus on the MDCK cells without the presence of silicon nitride.

Example 4: Evaluation of Influenza a Viricidal Activity by Silicon Nitride in MDCK Cells This study was designed to examine the antiviral capabilities of beta-silicon nitride (β-$Si_3N_4$) powder versus Influenza A at an incubation time-point of 30 minutes and a concentration of 15 wt. %/wt. A 15 wt. % suspension was prepared in 1.5 mL of virus diluted in DMEM with no additives.

A plaque assay methodology was utilized. To adequately quantify the plaque assay, the viability of Madin Darby Canine Kidney Cells (MDCK) were assessed as a function of exposure to various concentrations of $Si_3N_4$ for incubation periods ranging from 30 minutes to 72 hours. The results demonstrated that $Si_3N_4$ was completely viricidal to Influenza A with a reduction of >99.98% in viral load at the preselected conditions. The viability of the MDCK cells was found to be time- and dose-dependent. Essentially no loss in viability was observed for $Si_3N_4$ concentrations up to 15 wt. %/wt. Changes in viability were only noted for the 15 wt. % concentration at 24, 48, and 72 hours (i.e., 83.3%, 59.7%, and 44.0% viable, respectively).

Figure 17:
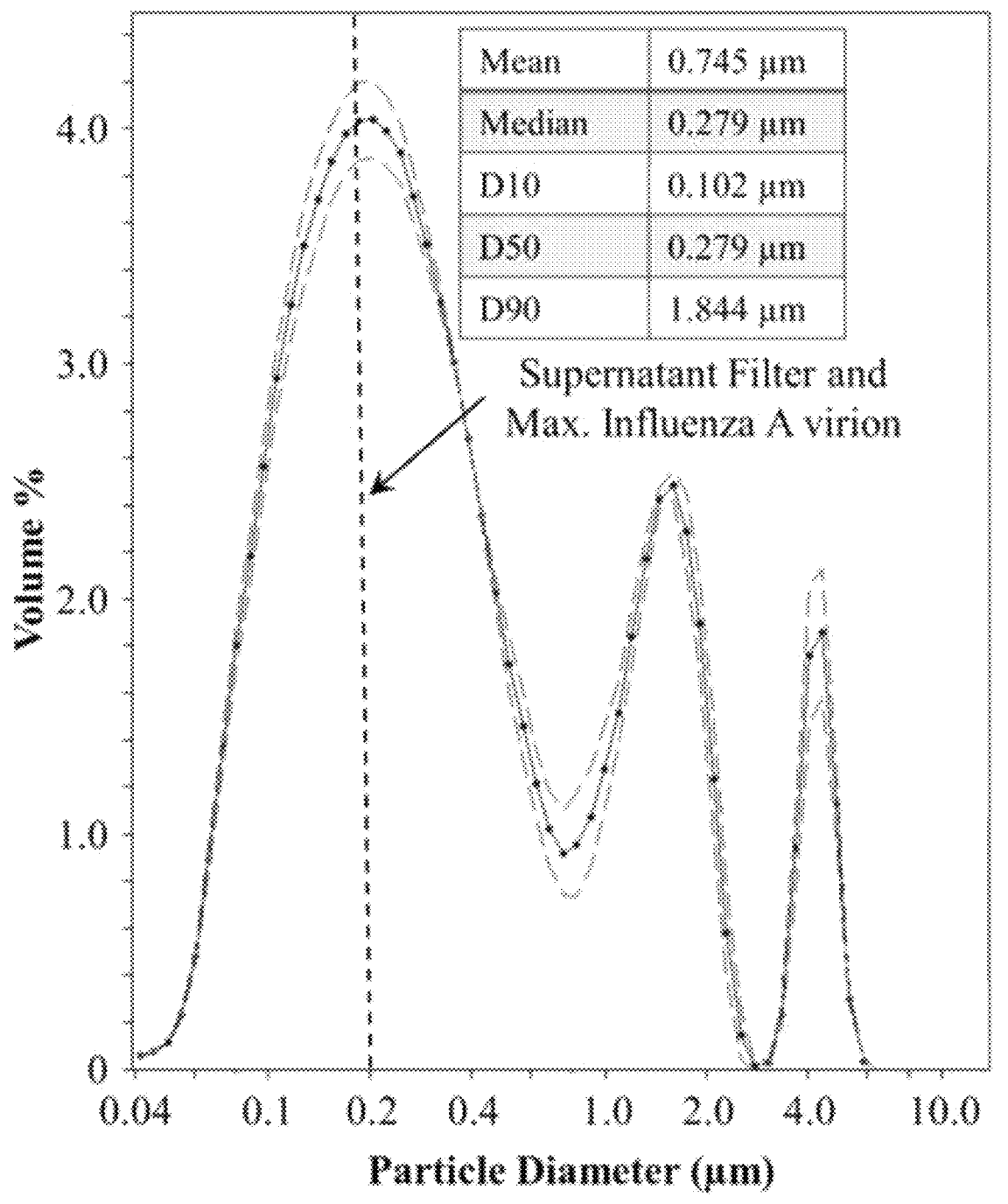

The $Si_3N_4$ powder used in this study had a nominal composition of 90 wt. % α-$Si_3N_4$, 6 wt. % yttria ($Y_2O_3$), and 4 wt. % alumina ($Al_2O_3$). It was prepared by aqueous mixing and spray-drying of the inorganic constituents, followed by sintering of the spray-dried granules (~1700° C. for ~3 h), hot-isostatic pressing (~1600° C., 2 h, 140 MPa in $N_2$), aqueous-based comminution, and freeze-drying. The resulting powder had a trimodal distribution with an average particle size of 0.8±1.0 μm as shown in FIG. 17. Doping $Si_3N_4$ with $Y_2O_3$ and $Al_2O_3$ is useful to densify the ceramic and convert it from its α- to p-phase during sintering. The mechanism of densification is via dissolution of α-phase and subsequent precipitation of p-phase grains facilitated by the formation of a transient intergranular liquid that solidifies during cooling. β-$Si_3N_4$ is therefore a composite composed of about 10 wt. % intergranular glass phase (IGP) and 90 wt. % crystalline β-$Si_3N_4$ grains.

Three sequential assays were conducted in this study: (1) An MDCK viability test; (2) An influenza A supernatant titration test with and without centrifugation and filtration; and (3) A viral titration using 15 wt. %/wt $Si_3N_4$ as the viral inhibitor for an incubation period of 30 m.

Figure 18:
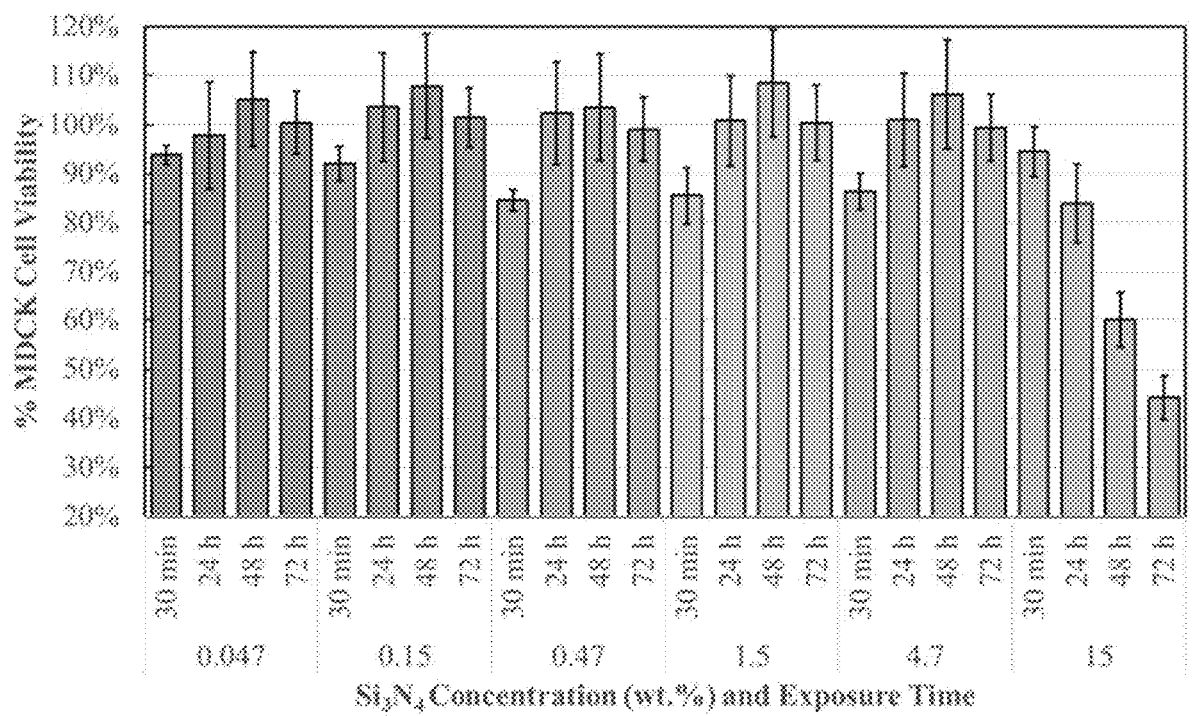
FIG. 18 shows the viability of the MDCK cells as function of $\beta$-$Si_3N_4$ concentration (wt. %/mL).

In FIG. 18, the viability of the MDCK cells is shown as function of β-$Si_3N_4$ concentration (wt. %/mL). Starting at 15 wt. %, serial dilutions were conducted to arrive at 0.047 wt. %. At the lower concentrations, cell viability was generally >80% for all timepoints up to 72 h. Note also that cell viability generally increased with exposure time for all concentrations except 15 wt. %. At 15 wt. % and 30-minutes exposure the cell viability was ~94.5%.

Following the determination of MDCK cell viability, twenty-four hours prior to the addition of the virus and sample to the cells, MDCK cells were plated in a 6-well plate at a density of $1\times10^6$ cells/well in a volume of 2 mL in Dulbecco's Minimum Essential Medium (DMEM) supplemented with 10% fetal bovine serum (FBS). On the day of the assay, triplicate samples of 15 wt. % of silicon nitride in virus diluted in DMEM with no additives at $1\times10^4$ PFU/mL was incubated for 30 minutes at room temperature with shaking. Following incubation, the samples were centrifuged for two minutes at 4° C. and 12,000 rpm, and further filtered through a 0.2-micron polyvinylidene difluoride (PVDF) filter. The samples were then serially diluted 1:5 and 7 concentrations were added to cells that had been washed 2 times with Dulbecco's Phosphate Buffered Saline (DPBS) in triplicate in a volume of 400 µL. The samples were incubated for 1 hour at 37° C. with rocking every 15 to 20 minutes. Following incubation, 2 mL of the plaque assay media was added to the wells and the cultures were incubated for 48 hours at 35° C./5% $CO_2$. After incubation, the cells were stained with crystal violet and the plaques were enumerated visually.

On the day of staining, the plaguing media was removed, and the monolayers were washed two times with DPBS. The cells were then fixed with 70% ethanol for 10 minutes at room temperature. The ethanol was removed, and 0.3% crystal violet solution was added to each well for 10 minutes at room temperature. Following this incubation, the crystal violet was removed, and the monolayers were washed two times with DPBS to remove residual crystal violet. The monolayers were air-dried overnight prior to counting the plaques.

Figure 19:
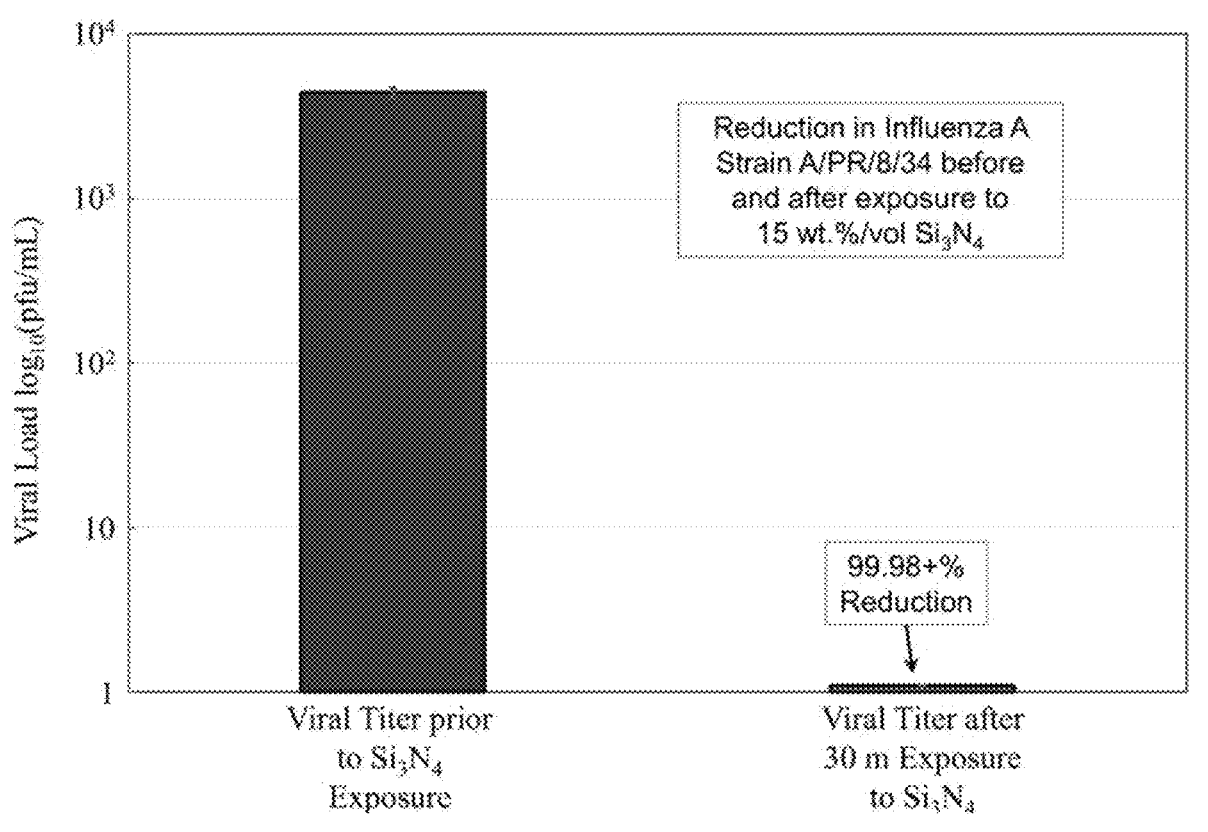

The viricidal test was conducted at a concentration of 15 wt. %/vol and at 30 min. The process steps of centrifugation and filtration only reduced the viral load by about 0.25 $\log_{10}$. Given this result, a subsequent titration was then conducted without and with the exposure of the virus to $Si_3N_4$ for 30 minutes. The concentration for the titration without $Si_3N_4$ was a priori selected to be $4.4\times10^3$ pfu/ml based on ISO 21702 (Measurement of antiviral activity on plastics and other non-porous surfaces). After 30 minutes of exposure to $Si_3N_4$, no plaques formed on the MDCK cells. $Si_3N_4$ was deemed to be 100% effective in inactivating Influenza A. A direct comparison of the viral titers before and after exposure to the $Si_3N_4$ powder for 30 m is provided in FIG. 19. The data clearly demonstrate >3.5 $\log_{10}$ reduction in viral load after exposure to $Si_3N_4$ (i.e., >99.98%).

In summary, these tests demonstrated that exposure of $Si_3N_4$ to MDCK cells had no adverse viability effects at concentrations less than 15 wt. %/vol or time periods of ≤30 minutes. At antiviral test conditions of 15 wt. %/vol $Si_3N_4$ at 30 minutes exposure at a viral load of $4.4\times10^3$ pfu/ml, $Si_3N_4$ inactivated essentially 100% of the exposed virions. $Si_3N_4$ was found to be viricidal to Influenza A under these conditions.

Example 5: Effect of α-$Si_3N_4$ Powder on MDCK Cells and Influenza A

α-$Si_3N_4$ powder was first evaluated for toxicity to MDCK cells following exposure for 30 minutes, 24 hours, 48 hours and 72 hours. A 15 weight % (wt. %) suspension was prepared in 1.5 mL of Dulbecco's Modified Eagle Medium (DMEM) supplemented with 2% fetal bovine serum (FBS).

Twenty-four hours prior to the addition of the sample to the cells, the α-$Si_3N_4$ powder suspension prepared as described above was incubated for 30 minutes at room temperature with shaking. Following the incubation, the suspension was centrifuged for two minutes at 4° C. at 12,000 rpm. The supernatant was further filtered through a 0.2-micron polyvinylidene difluoride (PVDF) filter and then serially diluted in 1/2-logarithmic increments. Six (6) concentrations were added to the pre-plated cells in triplicate in a volume of 200 µL. The plates were incubated for 30 minutes, 24, 48, and 72 hours at which time the cells were evaluated for cellular toxicity using the tetrazolium dye XTT (2,3-bis(2-methoxy-4-nitro-5-sulfophenyl)-5-[(phenylamino)carbonyl]-2H-tetrazolium hydroxide), as described below.

TC50 values for the test materials were derived by measuring the reduction of the tetrazolium dye XTT. XTT in metabolically active cells is metabolized by the mitochondrial enzyme NADPH oxidase to a soluble formazan product. XTT solution was prepared daily as a stock of 1 mg/mL in DMEM without additives. Phenazine methosulfate (PMS) solution was prepared at 0.15 mg/mL in Dulbecco's Phosphate Buffered Saline (DPBS) and stored in the dark at −20° C. XTT/PMS stock was prepared immediately before use by adding 40 µL of PMS per mL of XTT solution. Fifty µL (50 4) of XTT/PMS was added to each well of the plate and the plate incubated for 4 hours at 37° C. The 4-hour incubation has been empirically determined to be within the linear response range for XTT dye reduction with the indicated numbers of cells for each assay. The plates were sealed and inverted several times to mix the soluble formazan product and the plate was read at 450 nm (650 nm reference wavelength) with a Molecular Devices SpectraMax Plus 384 96 well plate format spectrophotometer.

Figure 20:
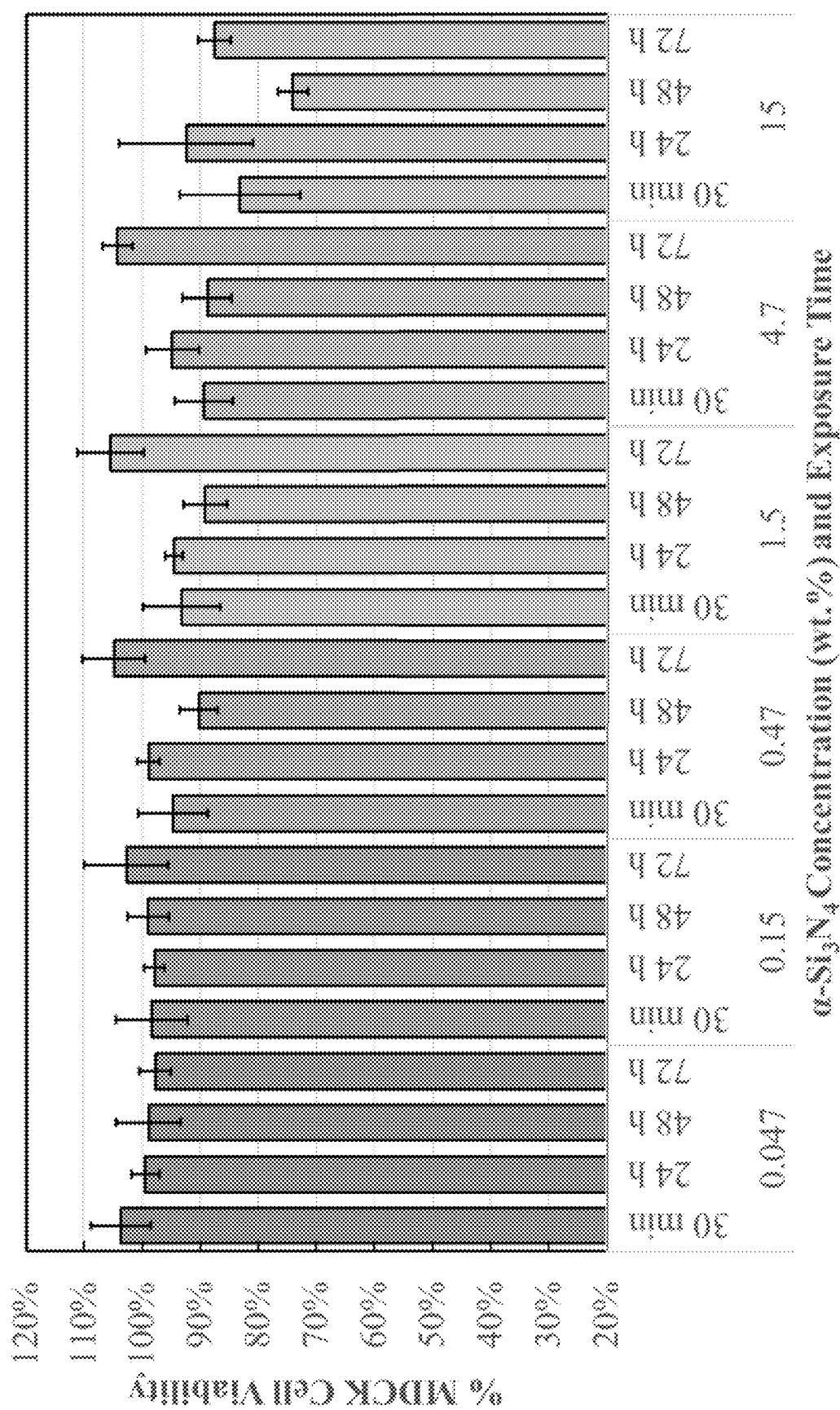
FIG. 20 shows the viability of the MDCK cells as function of $\alpha$-$Si_3N_4$ concentration (wt. %/mL).

MDCK cells were treated with 6 concentrations of the α-$Si_3N_4$ powder ranging from 15 wt. % to 0.047 wt. % for 30 minutes, 24 hours, 48 hours and 72 hours. In FIG. 20, the viability of the MDCK cells is shown as function of α-$Si_3N_4$ concentration (wt. %/mL). Following 30 minutes of exposure cells treated with all concentrations had viability greater than 90% except for cells treated with 4.7 wt. % and 15 wt. % which had 89% and 83% viability, respectively. At 24 hours viability of cell treated with each concentration remained above 92%. At 48 hours viability dropped below 90% in cells treated with 1.5 wt. %, 4.7 wt. % and 15 wt. % (89.1%, 88.7% and 74.0%, respectively) but at 72 hours only cells treated with 15 wt. % had viability below 90% (87.5%).

α-$Si_3N_4$ powder at 15 wt. % was then evaluated for virucidal activity against Influenza A strain A/PR/8/34 in MDCK cells. A 15 wt. % suspension was prepared in 1.5 mL of virus diluted in DMEM with no additives.

Twenty-four hours prior to the addition of the virus and sample to the cells, MDCK cells were plated in a 6-well plate at a density of $1\times10^6$ cells/well in a volume of 2 mL in Dulbecco's Minimum Essential Medium (DMEM) supplemented with 10% fetal bovine serum (FBS). On the day of the assay, triplicate samples of 15 wt. % of α-$Si_3N_4$ in virus diluted in DMEM with no additives at $1\times10^4$ PFU/mL was incubated for 30 minutes at room temperature with shaking. Following incubation, the samples were centrifuged for two minutes at 4° C. and 12,000 rpm, and further filtered through a 0.2-micron polyvinylidene difluoride (PVDF) filter. The samples were then serially diluted 1:5 and 7 concentrations were added to cells that had been washed 2 times with Dulbecco's Phosphate Buffered Saline (DPBS) in triplicate in a volume of 400 mL. The samples were incubated for 1 hour at 37° C. with rocking every 15 to 20 minutes. Following incubation, 2 mL of the plaque assay media was added to the wells and the cultures were incubated for 48 hours at 35° C./5% $CO_2$. After incubation, the cells were stained with crystal violet and the plaques were enumerated visually.

On the day of staining, the plaquing media was removed, and the monolayers were washed two times with DPBS. The cells were then fixed with 70% ethanol for 10 minutes at room temperature. The ethanol was removed, and 0.3% crystal violet solution was added to each well for 10 minutes at room temperature. Following this incubation, the crystal violet was removed, and the monolayers were washed two times with DPBS to remove residual crystal violet. The monolayers were air-dried overnight prior to counting the plaques.

The virucidal activity of 15 wt. % $\alpha$-$Si_3N_4$ powder was evaluated against Influenza virus A strain A/PR8/34 in MDCK cells. The target virus titer was $1 \times 10^4$ PFU/mL and the actual individual replicates were $3.1 \times 10^3$, $3.8 \times 10^3$, and $4.7 \times 10^3$ PFU/mL yielding a mean titer (and standard deviation) of $3.9 \times 10^3 \pm 0.8 \times 10^3$ PFU/mL. This actual titer is within two-fold of the targeted PFU/mL. The $\alpha$-$Si_3N_4$ powder treated samples had one well with a single plaque which resulted in a PFU/mL of 4.1.

Figure 21:
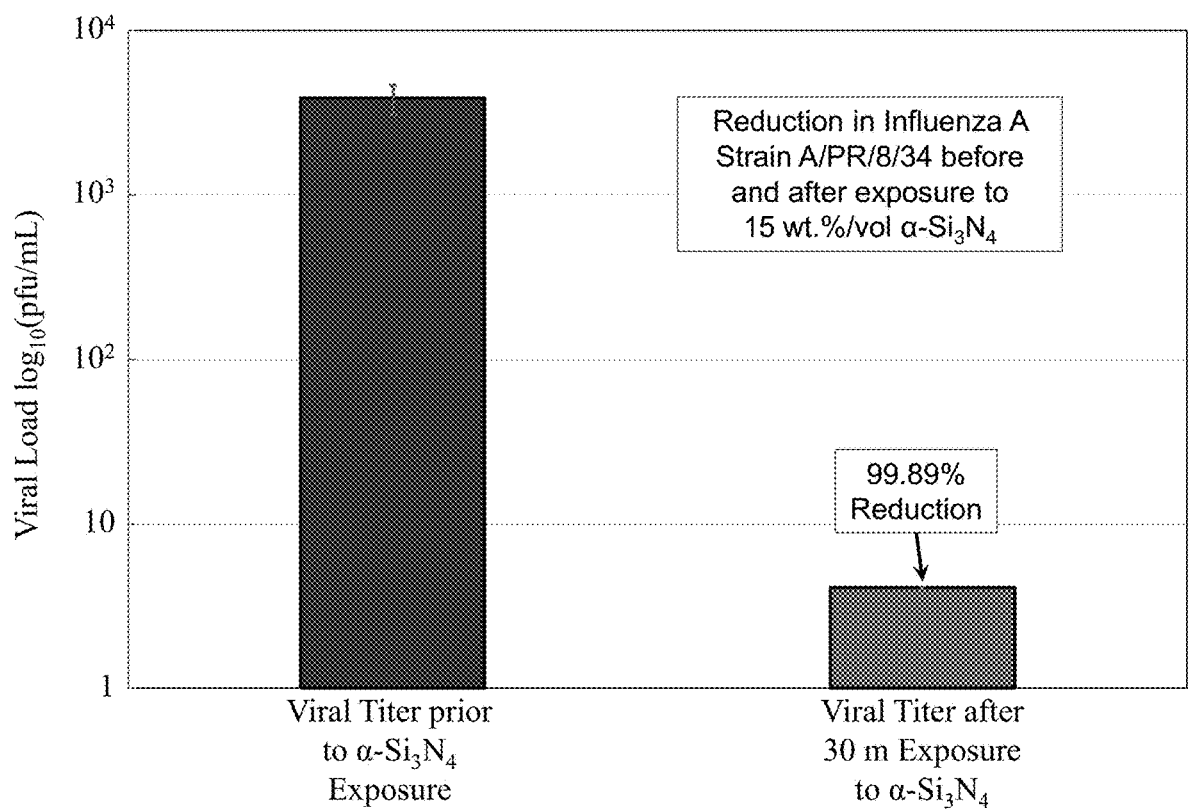
FIG. 21 shows a comparison of the viral titers before and after exposure of Influenza A to the $\alpha$-$Si_3N_4$ powder for 30 minutes.

The log reduction was 2.98 and was calculated using the following equation: $\log_{10}(A/B)$ where A is untreated virus and B is treated virus. The percent reduction was 99.89% and was calculated using the following equation: (A-B)×100/A where A is untreated virus and B is treated virus. A comparison of the viral titers before and after exposure to the $\alpha$-$Si_3N_4$ powder for 30 m is provided in FIG. 21. Therefore, the $\alpha$-$Si_3N_4$ powder at 15 wt. % was virucidal to influenza A virus strain A/PR/8/34 following a 30-minute exposure.

Example 6: Influenza a Virucidal Activity by Two Forms of $Si_3N_4$ Powder in MDCK Cells A 5 and 10 wt. % suspension of $\alpha$-$Si_3N_4$ and $\beta$-$Si_3N_4$ powder was prepared in 1.5 mL of virus diluted in DMEM with no additives.

Twenty-four hours prior to the addition of the virus and sample to the cells, MDCK cells were plated in a 6-well plate at a density of $1 \times 10^6$ cells/well in a volume of 2 mL in Dulbecco's Minimum Essential Medium (DMEM) supplemented with 10% fetal bovine serum (FBS). On the day of the assay, triplicate samples of 10 and 5 wt. % of $\alpha$-$Si_3N_4$ and $\beta$-$Si_3N_4$ powders in virus diluted in DMEM with no additives at $1 \times 10^4$ PFU/mL were incubated for 30 minutes at room temperature with shaking. Following incubation, the samples were centrifuged for two minutes at 4° C. and 12,000 rpm, and further filtered through a 0.2-micron polyvinylidene difluoride (PVDF) filter. The samples were then serially diluted 1:5 and 7 concentrations were added to cells that had been washed 2 times with Dulbecco's Phosphate Buffered Saline (DPBS) in triplicate in a volume of 400 μL. The samples were incubated for 1 hour at 37° C. with rocking every 15 to 20 minutes. Following incubation, 2 mL of the plaque assay media was added to the wells and the cultures were incubated for 48 hours at 35° C./5% $CO_2$. After incubation, the cells were stained with crystal violet and the plaques were enumerated visually.

On the day of staining, the plaquing media was removed, and the monolayers were washed two times with DPBS. The cells were then fixed with 70% ethanol for 10 minutes at room temperature. The ethanol was removed, and 0.3% crystal violet solution was added to each well for 10 minutes at room temperature. Following this incubation, the crystal violet was removed, and the monolayers were washed two times with DPBS to remove residual crystal violet. The monolayers were air-dried overnight prior to counting the plaques.

The virucidal activity of 5 and 10 wt. % of $\alpha$-$Si_3N_4$ and $\beta$-$Si_3N_4$ powder was evaluated against Influenza virus A strain AIPR8/34 in MDCK cells. This was performed in four individual experiments. The target virus titer was $1 \times 10^4$ PFU/mL.

In the first experiment the individual replicates for the untreated virus samples were $5.3 \times 10^3$, $5.9 \times 10^3$, and $4.1 \times 10^3$ PFU/mL yielding a mean titer (and standard deviation) of $5.1 \times 10^3 \pm 0.9 \times 10^3$ PFU/mL. Virus treated with 5 wt. % and 10 wt. % of $\beta$-$Si_3N_4$ for 10 minutes resulted in a PFU/mL of <21 for the virus treated with 10 wt. % and a PFU/mL of 21 (1 plaque formed) in virus treated with 5 wt. %. In this sample, the log reduction was 2.4 and was calculated using the following equation: log 10(NB) where A is untreated virus and B is treated virus. The percent reduction was 99.5% and was calculated using the following equation: (A–B)×100/A where A is untreated virus and B is treated virus.

In the second experiment the individual replicates for the untreated virus samples were $7.5 \times 10^3$, $7.2 \times 10^3$, and $5.0 \times 10^3$ PFU/mL yielding a mean titer (and standard deviation) of $6.6 \times 10^3 \pm 1.4 \times 10^3$ PFU/mL. Virus treated with 5 wt. % and 10 wt. % of $\beta$-$Si_3N_4$ for 5 minutes resulted in a PFU/mL of <21 for both.

In the third experiment the individual replicates were $6.9 \times 10^3$, $7.8 \times 10^3$, and $5.0 \times 10^3$ PFU/mL yielding a mean titer (and standard deviation) of $6.6 \times 10^3 \pm 1.4 \times 10^3$ PFU/mL. Virus treated with 5 wt. % and 10 wt. % of $\alpha$-$Si_3N_4$ for 10 minutes resulted in a PFU/mL of <21 for both.

In the fourth experiment the individual replicates were $8.8 \times 10^3$, $1.0 \times 10^4$, and $7.5 \times 10^3$ PFU/mL yielding a mean titer (and standard deviation) of $8.8 \times 10^3 \pm 1.3 \times 10^3$ PFU/mL. Virus treated with 5 wt. % and 10 wt. % of $\alpha$-$Si_3N_4$ for 5 minutes resulted in a PFU/mL of <21 for both.

In each of the experiments the actual titer determined for the untreated virus control was with-in two-fold of the targeted PFU/mL. Virus treated with both $\alpha$-$Si_3N_4$ and $\beta$-$Si_3N_4$ powder at 5 and 10 wt. % for 5 and 10 minutes resulted in a PFU/mL of <1 (no plaques observed) with the exception of the $\beta$-$Si_3N_4$ powder treated sample at 5 wt. % for 10 minutes which had one well with a single plaque resulting in a PFU/mL of 21.

Example 7: Silicon Nitride Inactivation of SARS-CoV-2 In Vitro

Figure 22:
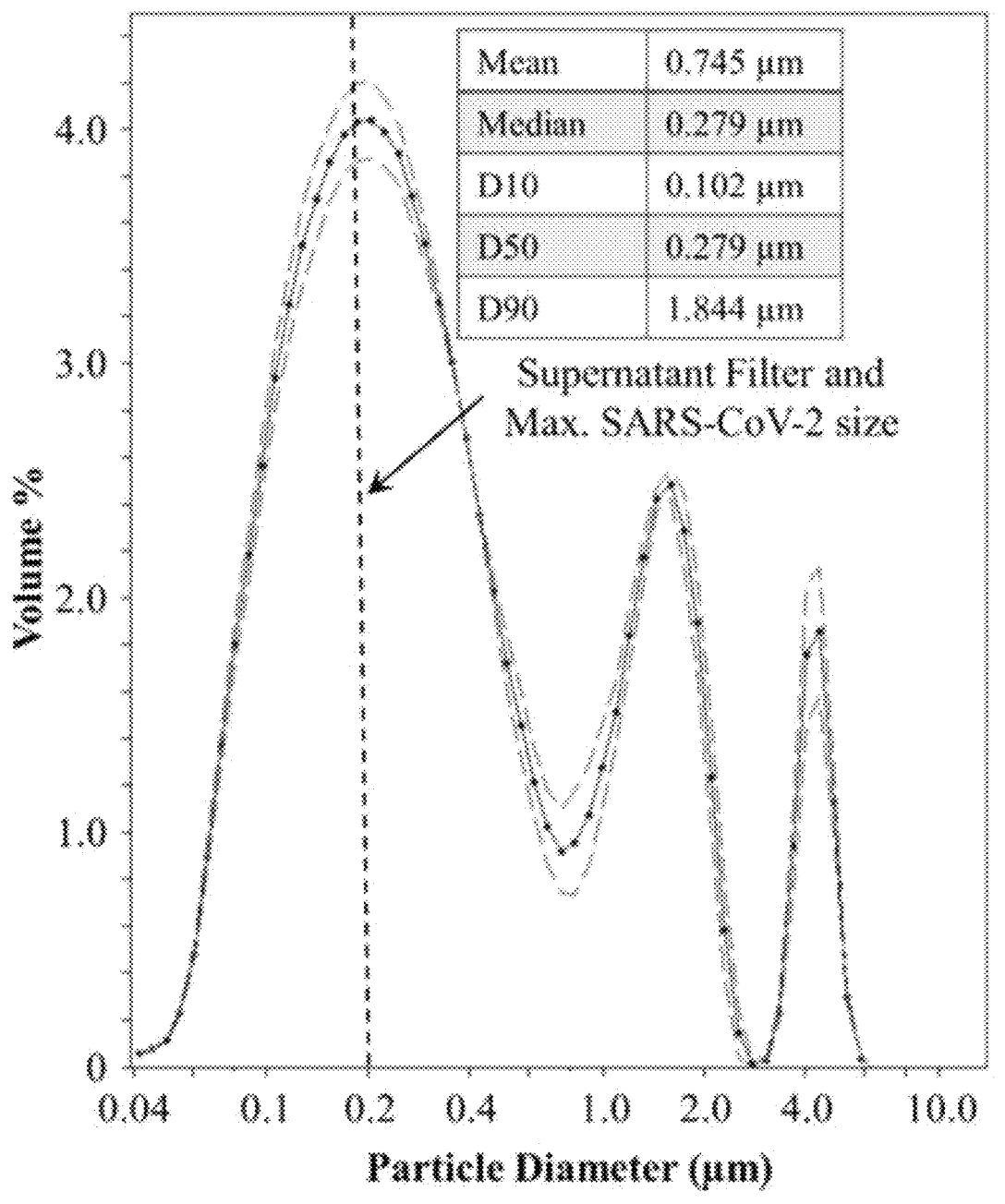

A doped $Si_3N_4$ powder ($\beta$-SiYAlON) with a nominal composition of 90 wt. % $\alpha$-$Si_3N_4$, 6 wt. % yttria ($Y_2O_3$), and 4 wt. % alumina ($Al_2O_3$) was prepared by aqueous mixing and spray-drying of the inorganic constituents, followed by sintering of the spray-dried granules (~1700° C. for ~3 h), hot-isostatic pressing (~1600° C., 2 h, 140 MPa in $N_2$), aqueous-based comminution, and freeze-drying. The resulting powder had a trimodal distribution with an average particle size of 0.8±1.0 μm as shown in FIG. 22. Doping $Si_3N_4$ with $Y_2O_3$ and $Al_2O_3$ densified the ceramic and converted it from its $\alpha$- to $\beta$-phase during sintering. The mechanism of densification is via dissolution of $\alpha$-phase and subsequent precipitation of $\beta$-phase grains facilitated by the formation of a transient intergranular liquid that solidifies during cooling. β-$Si_3N_4$ is therefore a composite composed of about 10 wt. % intergranular glass phase (IGP) and 90 wt. % crystalline β-$Si_3N_4$ grains.

Vero green African monkey kidney epithelial cells were chosen for this analysis due to their ability to support high levels of SARS-CoV-2 replication and their use in antiviral testing. These cells were cultured in DMEM supplemented with 10% FBS, 1% L-glutamine, and 1% penicillin/streptomycin. Cells were maintained at 37° C. and 5% $CO_2$. SARS-CoV-2 isolate USA-WA1/2020 was obtained from BEI Resources. Vero cells were inoculated with SARS-CoV-2 (MOI 0.1) to generate viral stocks. Cell-free supernatants were collected at 72 hours post-infection and clarified via centrifugation at 10,000 rpm for 10 minutes and filtered through a 0.2 μm filter. Stock virus was titered according to the plaque assay protocol detailed below.

The $Si_3N_4$ powder was suspended in 1 mL DMEM growth media in microcentrifuge tubes. Tubes were vortexed for 30 seconds to ensure adequate contact and then placed on a tube revolver for either 1, 5, or 10 minutes. At each time point, the samples were centrifuged, and the supernatant was collected and filtered through a 0.2 μm filter. Clarified supernatants were added to cells for either 24 or 48 hours. Untreated cells were maintained alongside as controls. Cells were tested at each time point using CellTiter Glo, which measures ATP production, to determine cell viability.

SARS-CoV-2 was diluted in DMEM growth media to a concentration of $2\times10^4$ PFU/mL. Four mL of the diluted virus was added to tubes containing silicon nitride at 20, 15, 10, and 5% (w/v). The virus without $Si_3N_4$ was processed in parallel as a control. Tubes were vortexed for 30 seconds to ensure adequate contact and then placed on a tube revolver for either 1, 5, or 10 minutes, while a virus only control was incubated for the maximum 10 minutes. At each time point, the samples were centrifuged, and the supernatant was collected and filtered through a 0.2 μm filter. The remaining infectious virus in the clarified supernatant was quantitated by plaque assay. An overview of the antiviral testing method is provided in FIG. 23. In step 1, SARS-CoV-2 virus was diluted in media. In step 2, 4 mL of diluted virus was added to tubes containing silicon nitride at 20, 15, 10, or 5% (w/v). In step 3, tubes were vortexed for 30 s to ensure adequate contact and the placed on a tube revolver for either 1 m, 5 m, or 10 m (virus only control was incubated for the maximum 10 m). In step 4, at each time point, the samples were centrifuged, and the supernatant was collected and filtered through a 0.2 μm filter. In step 5, clarified supernatant was used to perform plaque assays. Samples were serially diluted (10-fold) and added to fresh Vero for 1 h incubation, ricking every 15 min before adding an agarose medium overlay and incubating for 48 h. After 48 h incubation, cells were fixed with 10% FA and stained with Crystal Violet for counting.

Vero cells were plated at $2\times10^5$ cells/well in a 12-well plate on the day before the plaque assay. Clarified supernatants from the antiviral testing were serially diluted (10-fold) and 200 μL was added to Vero cells which were incubated for 1 hour at 37° C., 5% $CO_2$. Plates were rocked every 15 minutes to ensure adequate coverage and at 1 hour, a 1:1 ratio of 0.6% agarose and 2×EMEM supplemented with 5% FBS, 2% penicillin/streptomycin, 1% non-essential amino acids (VWR, Cat #45000-700), 1% sodium pyruvate, and 1% L-glutamine was added to the cells before incubating for 48 hours at 37° C., 5% $CO_2$. After incubation, the cells were fixed with 10% formaldehyde and stained with 2% crystal violet in 20% ethanol for counting.

Figure 24A:
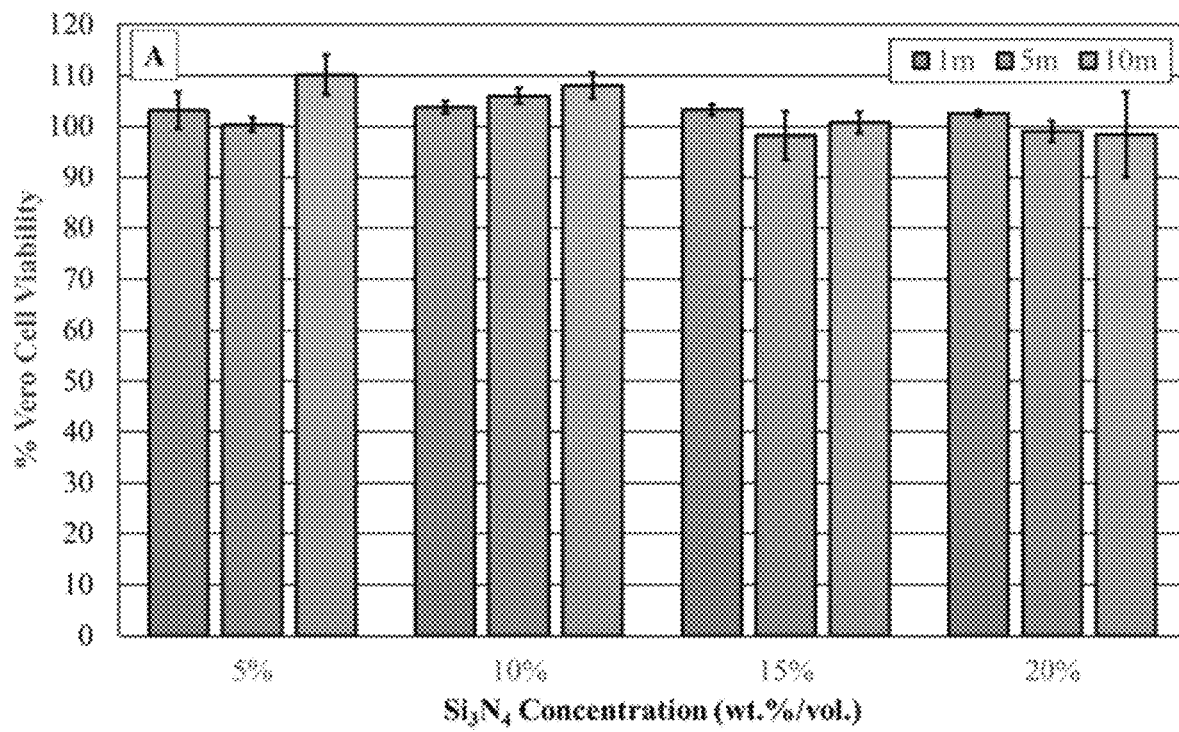
FIG. 24A shows Vero cell viability measured at 24 hours post-exposure to silicon nitride at concentrations of either 5, 10, 15 or 20 wt. %/vol (n=4) incubated with cell culture media for 1, 5, and 10 m.
Figure 24B:
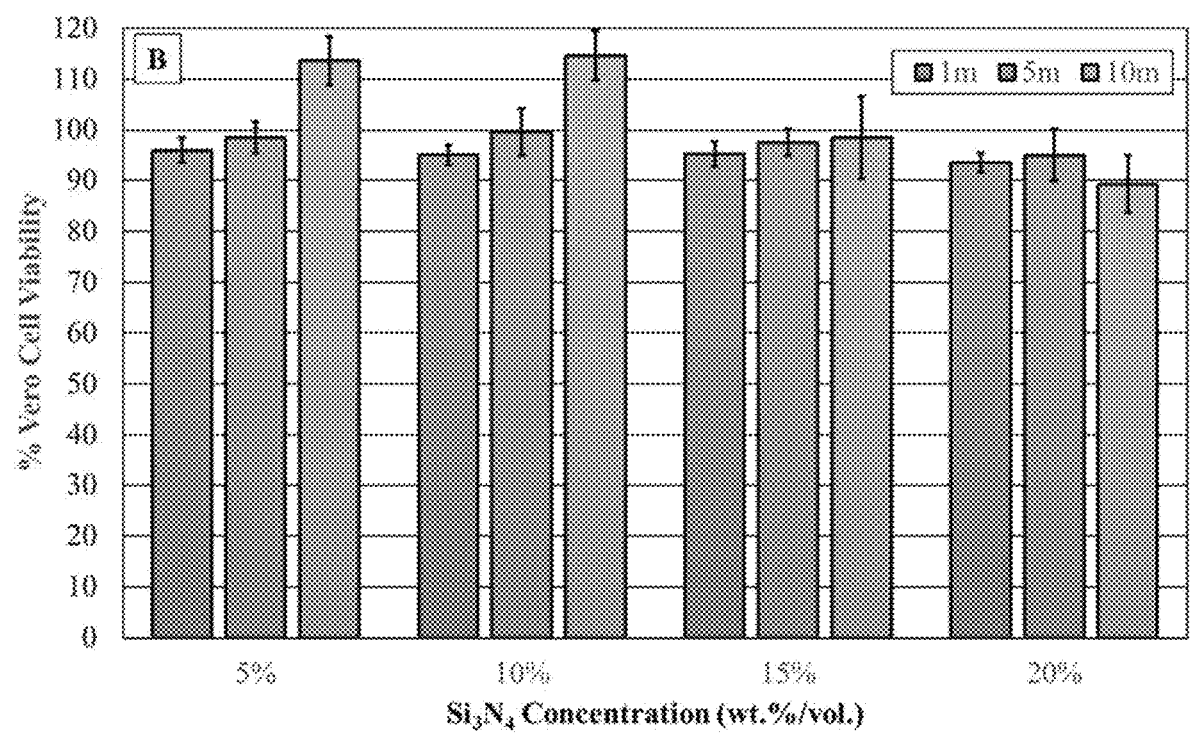
FIG. 24B shows Vero cell viability measured at 48 hours post-exposure to silicon nitride at concentrations of either 5, 10, 15 or 20 wt. %/vol (n=4) incubated with cell culture media for 1, 5, and 10 m.

The impact of $Si_3N_4$ on eukaryotic cell viability was tested. $Si_3N_4$ was resuspended in cell culture media at 5, 10, 15, and 20% (w/v). Samples were collected at 1, 5, and 10 minutes and added to Vero cells. Vero cell viability was measured at 24 and 48 hours post-exposure (FIGS. 24A and 24B). No significant decrease in cell viability was observed at either 24 or 48 hours post-exposure with 5%, 10%, or 15% silicon nitride. A small impact on cell viability (~10% decrease) was observed at 48 hours in cells exposed to 20% $Si_3N_4$. Interestingly, a ~10% increase in Vero cell viability was observed at 48 hours with the 5%-10 minute and 10%-10 minute samples (FIG. 24B), suggesting that $Si_3N_4$ may be stimulating cell growth or cellular metabolism under these conditions. These data indicated that $Si_3N_4$ has minimal impact on Vero cell health and viability up to 20 wt. %/vol.

Figure 25A:
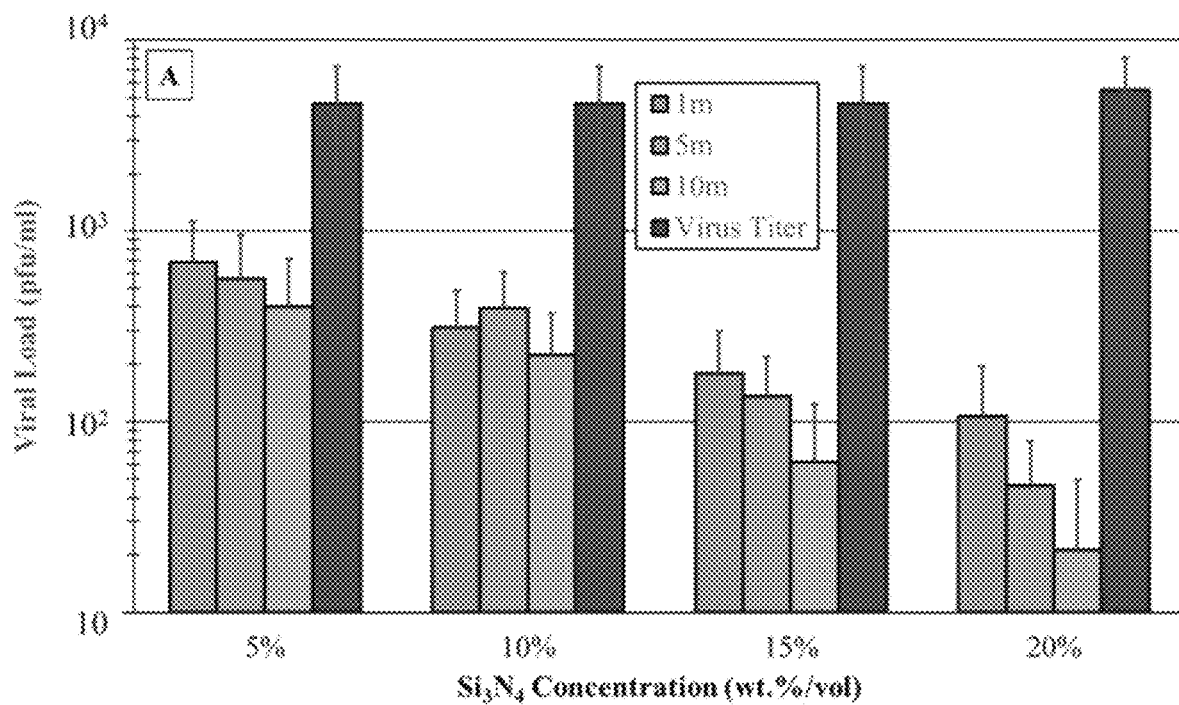
FIG. 25A shows titers of silicon nitride at concentrations of 5, 10, 15, and 20 wt. %/vol incubated with SARS-CoV-2 virus diluted in cell culture media for 1, 5, and 10 m expressed as PFU/mL.
Figure 25B:
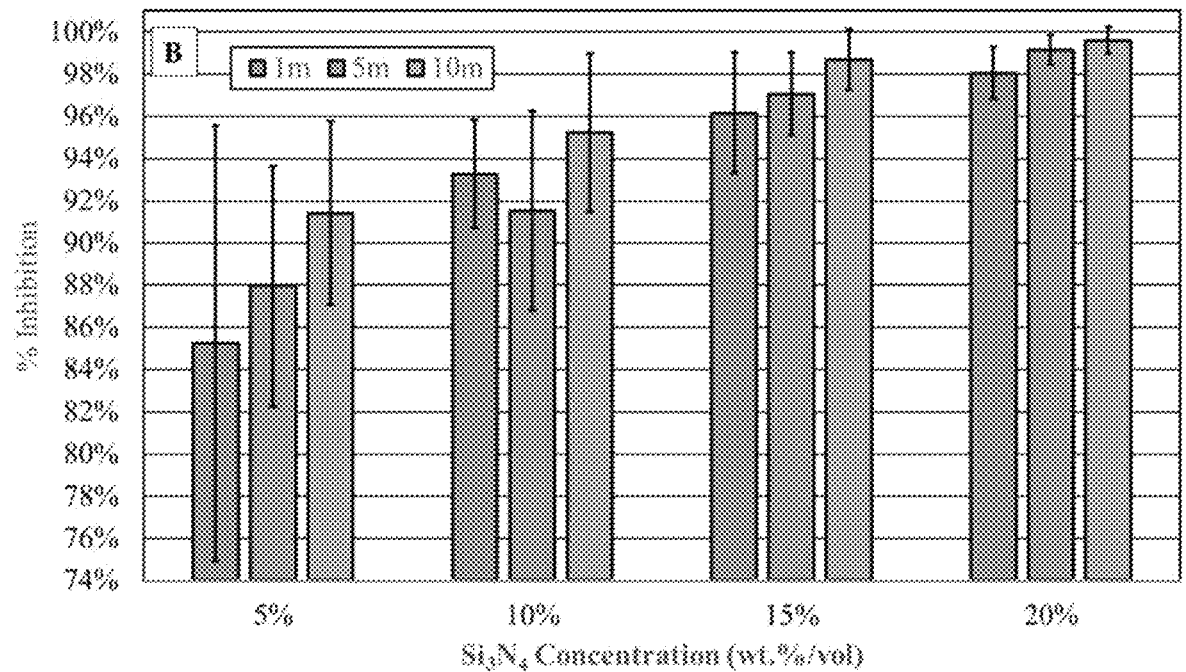
FIG. 25B shows titers of silicon nitride at concentrations of 5, 10, 15, and 20 wt. %/vol incubated with SARS-CoV-2 virus diluted in cell culture media for 1, 5, and 10 m expressed as % inhibition.

Given that 5, 10, 15, and 20% $Si_3N_4$ were non-toxic to Vero cells, antiviral testing at these concentrations was performed. SARS-CoV-2 virions were exposed to $Si_3N_4$ at these concentrations for 1, 5, or 10 minutes. Following $Si_3N_4$ exposure, the infectious virus remaining in each solution was determined through plaque assay. At each timepoint, the samples were centrifuged, and the supernatant was collected and filtered through a 0.2 um filter. The clarified supernatant was used to perform plaque assay in duplicate. Virus processed in parallel but only exposed to cell culture media contained $4.2\times10^3$ PFU/mL. SARS-CoV-2 titers were reduced when exposed to all concentrations of $Si_3N_4$ tested (FIGS. 25A and 25B). The inhibition was dose-dependent with SARS-CoV-2 exposed for 1 minute and 5% $Si_3N_4$ having reduced viral titers by ~0.8 $log_{10}$, 10% $Si_3N_4$ by ~1.2 $log_{10}$, 15% $Si_3N_4$ by 1.4 $log_{10}$, and 20% $Si_3N_4$ by 1.7 $log_{10}$ (FIG. 25A). Similar results were observed with the 5 and 10 minute samples. This reduction in viral titers corresponded to 85% viral inhibition at 5% $Si_3N_4$, 93% at 10% $Si_3N_4$, 96% at 15% $Si_3N_4$, and 98% viral inhibition at 20% $Si_3N_4$ (FIG. 25B). Higher $Si_3N_4$ concentrations for longer times resulted in increased inhibition—leading to 99.6% viral inhibition at 20% $Si_3N_4$ and 10 minute exposure (FIG. 25B). These data indicate that $Si_3N_4$ has a strong antiviral effect against SARS-CoV-2.

The surprising finding was that a one-minute exposure to a 5% solution of $Si_3N_4$ resulted in 85% inactivation of SARS-CoV-2, while Vero cell viability was minimally impacted even after a 48 hour exposure to a 20% concentration of the same material.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. An antiviral composition comprising silicon nitride powder at a concentration of 1 wt. % to 15 wt. %, wherein the powder has an average particle size of 0.6 μm to 5 μm, wherein the silicon nitride inactivates at least 99% of a human virus in contact with the composition for at least 30 minutes, and wherein the human virus is not SARS-CoV-2.

2. The antiviral composition of claim 1, wherein the silicon nitride is present at a concentration of less than or equal to 10 wt. %.

3. The antiviral composition of claim 1, wherein the silicon nitride comprises $\alpha$-$Si_3N_4$, $\beta$-$Si_3N_4$, SiYAlON, $\beta$-SiYAlON, SiYON, or SiAlON.

4. The antiviral composition of claim 1, wherein the composition comprises a slurry, suspension, gel, spray, paint, or toothpaste.

5. The antiviral composition of claim 4, wherein the composition comprises a toothpaste and the silicon nitride is in the form of a powder that is directly substituted for silicon dioxide powder found in standard toothpaste.

6. An antiviral apparatus comprising silicon nitride powder at a concentration of 1 wt. % to 15 wt. %, wherein the powder has an average particle size of 0.6 μm to 5 μm, wherein the silicon nitride inactivates at least 99% of a human virus in contact with the apparatus for at least 30 minutes, and wherein the human virus is not SARS-CoV-2.

7. The antiviral apparatus of claim 6, wherein the silicon nitride is present at a concentration of less than or equal to 10 wt. %.

8. The antiviral apparatus of claim 6, wherein the silicon nitride comprises $\alpha$-$Si_3N_4$, $\beta$-$Si_3N_4$, SiYAlON, $\beta$-SiYAlON, SiYON, or SiAlON.

9. The antiviral apparatus of claim 6, wherein the antiviral apparatus is a medical device, medical equipment, an examination table, a filter, a mask, a glove, a catheter, an endoscopic instrument, or a commonly-touched surface.

10. The antiviral apparatus of claim 6, wherein the apparatus comprises a substrate having a metallic composition, a polymeric composition, and/or a ceramic composition and the silicon nitride is coated on or embedded in a surface of the substrate.

11. A method of decreasing transmission of a human virus comprising:
    contacting an antiviral apparatus with the human virus for at least 30 minutes,
    wherein the antiviral apparatus comprises silicon nitride powder at a concentration of 1 wt. % to 15 wt. %, wherein the powder has an average particle size of 0.6 μm to 5 μm,
    wherein the silicon nitride inactivates at least 99% of the virus in contact with the antiviral apparatus, and
    wherein the human virus is not SARS-CoV-2.

12. The method of claim 11, wherein the silicon nitride is present at a concentration of less than or equal to 10 wt. %.

13. The method of claim 11, wherein the silicon nitride comprises $\alpha$-$Si_3N_4$, $\beta$-$Si_3N_4$, SiYAlON, $\beta$-SiYAlON, SiYON, or SiAlON.

* * * * *